(12) United States Patent
Yamato et al.

(10) Patent No.: US 10,079,346 B2
(45) Date of Patent: Sep. 18, 2018

(54) HETEROAROMATIC COMPOUNDS FOR ORGANIC ELECTRONICS

(71) Applicant: BASF SE, Ludwigshafen (DE)

(72) Inventors: Hitoshi Yamato, Takarazuka (JP); Takuya Tsuda, Amagasaki (JP); Chao Wu, Mannheim (DE); Thomas Weitz, Munich (DE); Michael Eustachi, Walldorf (DE); Maximilian Hemgesberg, Kaiserslautern (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/537,522

(22) PCT Filed: Dec. 16, 2015

(86) PCT No.: PCT/EP2015/079966
§ 371 (c)(1),
(2) Date: Jun. 19, 2017

(87) PCT Pub. No.: WO2016/096967
PCT Pub. Date: Jun. 23, 2016

(65) Prior Publication Data
US 2017/0365791 A1 Dec. 21, 2017

(30) Foreign Application Priority Data
Dec. 19, 2014 (EP) .................................. 14199287

(51) Int. Cl.
*C07D 513/14* (2006.01)
*H01L 51/00* (2006.01)
*H01L 51/05* (2006.01)

(52) U.S. Cl.
CPC ........ *H01L 51/0071* (2013.01); *C07D 513/14* (2013.01); *H01L 51/0562* (2013.01)

(58) Field of Classification Search
CPC ............ H01L 51/0071; H01L 51/0562; C07D 513/14
USPC ........................................................ 544/14
See application file for complete search history.

(56) References Cited

PUBLICATIONS

International Search Report and Written Opinion dated Feb. 9, 2016 in PCT/EP2015/079966.
International Preliminary Report on Patentability and Written Opinion dated Jun. 29, 2017 in PCT/EP2015/079966.
Extended European Search Report dated Mar. 26, 2015 in Patent Application No. 14199287.5.
Wei Hong et al., "Synthesis and Properties of Heteroacenes Containing Pyrrole and Thiazine Rings as Promising n-Type Organic Semiconductor Candidates", Chinese Journal of Chemistry, 2009, pp. 846-849.
Wei Hong et al., "6H-Pyrrolo[3,2-b:4,5-b']bis[1,4]benzothiazines: Facilely Synthesized Semiconductors for Organic Field-Effect Transistors", Journal of Materials Chemistry, 2008, pp. 4814-4820.
Zhongming Wei et al., "Organic Single Crystal Field-Effect Transistors Based on 6H-pyrrolo[3,2-b:4,5-b']bis[1,4]benzothiazine and its Derivatives", Advanced Materials, vol. 22, No. 22, XP002737232, 2010, pp. 2458-2468.

*Primary Examiner* — Kahsay Habte
(74) *Attorney, Agent, or Firm* — Oblon, McClelland, Maier & Neustadt, L.L.P.

(57) ABSTRACT

The present invention provides compounds of formula (I) wherein X is O, S or $NR^{10}$, wherein $R^{10}$ is H, $C_{1-30}$-alkyl, substituted $C_{1-30}$-alkyl, $C_{2-30}$-alkenyl, substituted $C_{2-30}$-alkenyl, $C_{2-30}$-alkynyl, substituted $C_{2-30}$-alkynyl or $C(O)\text{-}OR^{11}$, $R^1$ and $R^{11}$ are independently from each other selected from the group consisting of $C_{1-30}$-alkyl, substituted $C_{1-30}$-alkyl, $C_{2-30}$-alkenyl, substituted $C_{2-30}$-alkenyl, $C_{2-30}$-alkynyl, substituted $C_{2-30}$-alkynyl, $C_{5-8}$-cycloalkyl, substituted $C_{5-8}$-cycloalkyl, $C_{5-8}$-cycloalkenyl, and substituted $C_{5-8}$-cycloalkenyl, and an electronic device comprising the compounds as semiconducting material.

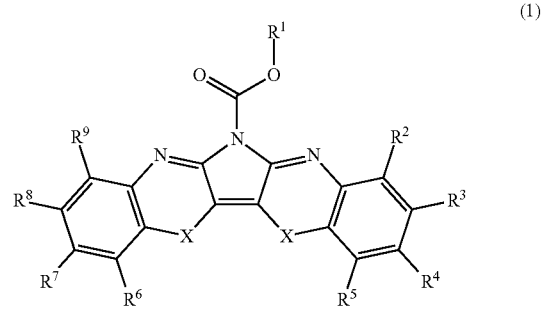

(I)

11 Claims, 5 Drawing Sheets

HETEROAROMATIC COMPOUNDS FOR ORGANIC ELECTRONICS

Organic semiconducting materials can be used in electronic devices such as organic photovoltaic devices (OPVs), organic field-effect transistors (OFETs), organic light emitting diodes (OLEDs), and organic electrochromic devices (ECDs).

For efficient and long lasting performance, it is desirable that the organic semiconducting material-based devices show high charge carrier mobility as well as high stability, in particular towards oxidation by air.

Furthermore, it is desirable that the organic semiconducting materials are compatible with liquid processing techniques such as spin coating as liquid processing techniques are convenient from the point of processability, and thus allow the production of low cost organic semiconducting material-based electronic devices. In addition, liquid processing techniques are also compatible with plastic substrates, and thus allow the production of light weight and mechanically flexible organic semiconducting material-based electronic devices.

The use of pyrrolobis(benzothiazines) as semiconducting material is known in the art.

Hong, W.; Wei, Z.; Xu, W.; Wang, Q.; Zho, D. Chinese Journal of Chemistry (2009), 27(4), 846-849 describes

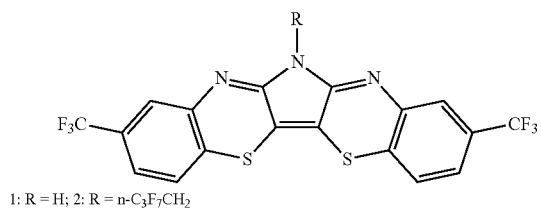

1: R = H; 2: R = n-C$_3$F$_7$CH$_2$ which are air-stable and promising n-type semiconducting materials for use in organic electronics.

Hong, W.; Wei, Z.; Xi, H.; Xu, W.; Hu, W.; Wang, Q. Zhu, D. J. Mater. Chem. 2008, 18, 4814-4820 describes

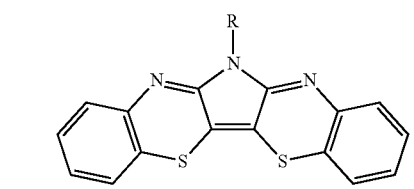

1: R = H; 2: R = Ph; 3: R = nC$_8$H$_{17}$ and field effect transistors comprising these compounds as p-type semiconducting compounds.

An organic field effect transistor comprising compound of formula 1 as semiconducting material shows a mobility of 0.34 cm$^2$ V$^{-1}$s$^{-1}$ (when deposited by vacuum deposition at 60° C. substrate temperature), but compound 1 was found to be only slightly soluble in THF, hot DMF and DMSO. An organic field effect transistor comprising compound of formula 2 as semiconducting material shows a mobility of only 1.77×10$^{-4}$ cm$^2$ V$^{-1}$s$^{-1}$ (when deposited by vacuum deposition at 60° C. substrate temperature), however compound 2 was found to very soluble in CH$_2$Cl$_2$. An organic field effect transistor comprising compound of formula 3 as semiconducting material shows a mobility of only 3.01×10-3 cm$^2$ V$^{-1}$s$^{-1}$ (when deposited by vacuum deposition at 60° C. substrate temperature), however compound 3 was found to very soluble in CH$_2$Cl$_2$.

Wei, Z.; Hong, W.; Geng, H.; Wang, C.; Liu, Y.; Li, R.; Xu, W.; Shuai, Z.; Hu, W.; Wang, Q., Zhu, D. Advanced Materials 22 (22), 2010, 2458 to 2468 also describes

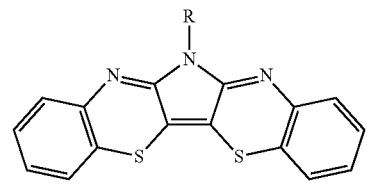

1: R = H; 2: R = Ph; 3: R = nC$_8$H$_{17}$ and field effect transistors comprising these compounds as p-type semiconducting compounds.

The disadvantage of the compound 1 is the low solubility in organic solvents. The disadvantages of compounds 2 and 3 is that organic field effect transistors comprising compounds 2 and 3 as semiconducting materials show low mobilities.

It was the object of the present invention to provide organic semiconducting materials, which show high solubility in organic solvents and high stability towards oxidation by air, and which at the same time, when applied as a layer in an organic electronic device, yield organic electronic devices showing good performance such as high charge carrier mobilities.

This object is solved by the compounds of claim 1, the process of claim 8, the electronic device of claim 9 and the use of claim 11.

The organic semiconducting materials of the present invention are compounds of formula

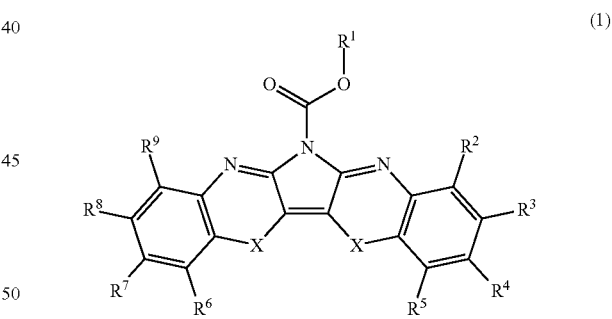

(1)

wherein
X is O, S or NR$^{10}$
wherein R$^{10}$ is H, C$_{1-30}$-alkyl, substituted C$_{1-30}$-alkyl, C$_{2-30}$-alkenyl, substituted C$_{2-30}$-alkenyl, C$_{2-30}$-alkynyl, substituted C$_{2-30}$-alkynyl or C(O)—OR$^{11}$,
R$^1$ and R$^{11}$ are independently from each other selected from the group consisting of C$_{1-30}$-alkyl, substituted C$_{1-30}$-alkyl, C$_{2-30}$-alkenyl, substituted C$_{2-30}$-alkenyl, C$_{2-30}$-alkynyl, substituted C$_{2-30}$-alkynyl, C$_{5-8}$-cycloalkyl, substituted C$_{5-8}$-cycloalkyl, C$_{5-8}$-cycloalkenyl, and substituted C$_{5-8}$-cycloalkenyl,
R$^2$, R$^3$, R$^4$, R$^5$, R$^6$, R$^7$, R$^8$ and R$^9$ are independently from each other selected from the group consisting of H, C$_{1-30}$-alkyl, substituted C$_{1-30}$-alkyl, C$_{2-30}$-alkenyl, substituted C$_{2-30}$-alkenyl, C$_{2-30}$-alkynyl, substituted C$_{2-30}$-alkynyl, $C_{5-8}$-cycloalkyl, substituted $C_{5-8}$-cycloalkyl, $C_{5-8}$-cycloalkenyl, substituted $C_{5-8}$-cycloalkenyl, O—$C_{1-30}$-alkyl, substituted O—$C_{1-30}$-alkyl, S—$C_{1-30}$-alkyl, substituted S—$C_{1-30}$-alkyl, $C_{6-14}$-aryl, substituted $C_{6-14}$-aryl, 5 to 15 membered heteroaryl, substituted 5 to 15 membered heteroaryl and halogen; or $R^2$ and $R^3$, $R^3$ and $R^4$, $R^4$ and $R^5$, $R^6$ and $R^7$, $R^7$ and $R^8$, or, $R^8$ and $R^9$ together with the C-atoms, to which they are connected, form a 6 to 10 membered aromatic ring system, substituted 6 to 10 membered aromatic ring system, 5 to 12 membered heteroaromatic ring system or a substituted 5 to 12 membered heteroaromatic ring system, wherein substituted $C_{1-30}$-alkyl, substituted $C_{2-30}$-alkenyl, substituted $C_{2-30}$-alkynyl, substituted O—$C_{1-30}$-alkyl and substituted S—$C_{1-30}$-alkyl, at each occurrence, are $C_{1-30}$-alkyl, $C_{2-30}$-alkenyl, $C_{2-30}$-alkynyl, O—$C_{1-30}$-alkyl, respectively, S—$C_{1-30}$-alkyl, which are substituted with at least one substituent independently selected from the group consisting of $C_{5-6}$-cycloalkyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—C(O)$R^b$, $NR^a$—C(O)—$OR^b$, $NR^a$—C(O)—$NR^bR^c$, $SR^a$, S—C(O)—$R^a$, halogen, CN, and $NO_2$;

substituted $C_{5-8}$-cycloalkyl, and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{2-20}$-alkenyl, $C_{2-20}$-alkynyl, $C_{5-6}$-cycloalkyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—C(O)$R^b$, $NR^a$—C(O)—$OR^b$, $NR^a$—C(O)—$NR^bR^c$, $SR^a$, S—C(O)—$R^a$, halogen, CN, and $NO_2$;

substituted $C_{6-14}$-aryl, substituted 5 to 15 membered heteroaryl, substituted 6 to 10 membered aromatic ring system, and substituted 5 to 12 membered heteroaromatic ring system, at each occurrence, are $C_{6-14}$-aryl, 5 to 15 membered heteroaryl, 6 to 10 membered aromatic ring system, respectively, 5 to 12 membered heteroaromatic ring system, which are substituted with at least one substituent independently selected from the group consisting of $C_{1-20}$-alkyl, $C_{2-20}$-alkenyl, $C_{2-20}$-alkynyl, $C_{5-6}$-cycloalkyl, $C_{5-6}$-cycloalkenyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—C(O)$R^b$, $NR^a$—C(O)—$OR^b$, $NR^a$C(O)—$NR^bR^c$, $SR^a$, S—C(O)—$R^a$, halogen, CN, and $NO_2$, wherein at least one $CH_2$-group, but not adjacent $CH_2$-groups, of $C_{1-30}$-alkyl, substituted $C_{1-30}$-alkyl, $C_{2-30}$-alkenyl, substituted $C_{2-30}$-alkenyl, $C_{2-30}$-alkynyl, substituted $C_{2-30}$-alkynyl, $C_{5-8}$-cycloalkyl, substituted $C_{5-8}$-cycloalkyl, $C_{5-8}$-cycloalkenyl, substituted $C_{5-8}$-cycloalkenyl, O—$C_{1-30}$-alkyl, substituted O—$C_{1-30}$-alkyl, S—$C_{1-30}$-alkyl and substituted S—$C_{1-30}$-alkyl, can be replaced by a linking group selected from the group consisting of O, S, $NR^{12}$, CO, O—C(O), C(O)—O, O—C(O)—O, S—C(O), C(O)—S, $NR^{12}$—C(O), C(O)—$NR^{12}$, OC(O)—$NR^{12}$ and $NR^{12}$—C(O)—O, wherein $R^{12}$ is H, $C_{1-30}$-alkyl, substituted $C_{1-30}$-alkyl, $C_{2-30}$-alkenyl, substituted $C_{2-30}$-alkenyl, $C_{2-30}$-alkynyl, substituted $C_{2-30}$-alkynyl or C(O)—$OR^d$, $R^a$, $R^b$, $R^c$ and $R^d$ are independently from each other and at each occurrence selected from the group consisting of H, $C_{1-20}$-alkyl, $C_{2-20}$-alkenyl, $C_{2-20}$-alkynyl, $C_{5-6}$-cycloalkyl, $C_{5-6}$-cycloalkenyl, $C_{6-10}$-aryl, and 5 to 12 membered heteroaryl.

$C_{1-20}$-alkyl and $C_{1-30}$-alkyl can be branched or unbranched. Examples of $C_{1-20}$-alkyl are methyl, ethyl, n-propyl, isopropyl, n-butyl, sec-butyl, isobutyl, tert-butyl, n-pentyl, neopentyl, isopentyl, n-(1-ethyl)propyl, n-hexyl. n-heptyl, n-octyl, n-(2-ethyl)hexyl, n-nonyl, n-decyl, n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$). Examples of $C_{1-30}$-alkyl are $C_{1-20}$-alkyl and n-docosyl ($C_{22}$), n-tetracosyl ($C_{24}$), n-hexacosyl ($C_{26}$), n-octacosyl ($C_{28}$) and n-triacontyl ($C_{30}$).

$C_{2-20}$-alkenyl and $C_{2-30}$-alkenyl can be branched or unbranched. Examples of $C_{2-20}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl, docenyl, linoleyl ($C_{18}$), linolenyl ($C_{18}$), oleyl ($C_{18}$), and arachidonyl ($C_{20}$). Examples of $C_{2-30}$-alkenyl are $C_{2-20}$-alkenyl and erucyl ($C_{22}$).

$C_{2-20}$-alkynyl and $C_{2-30}$-alkynyl can be branched or unbranched. Examples of $C_{2-20}$-alkynyl and $C_{2-30}$-alkynyl are ethynyl, 2-propynyl, 2-butynyl, 3-butynyl, pentynyl, hexynyl, heptynyl, octynyl, nonynyl, decynyl, undecynyl, dodecynyl, undecynyl, dodecynyl, tridecynyl, tetradecynyl, pentadecynyl, hexadecynyl, heptadecynyl, octadecynyl, nonadecynyl and icosynyl ($C_{20}$).

Examples of $C_{5-6}$-cycloalkyl are cyclopentyl and cyclohexyl. Examples of $C_{5-8}$-cycloalkyl are $C_{5-6}$-cycloalkyl and cycloheptyl and cyclooctyl.

Examples of $C_{5-6}$-cycloalkenyl are cyclopentenyl and cyclohenexyl. Examples of $C_{5-8}$-cycloalkenyl are $C_{5-6}$-cycloalkenyl and cycloheptenyl and cyclooctenyl.

Examples of $C_{6-10}$-aryl are

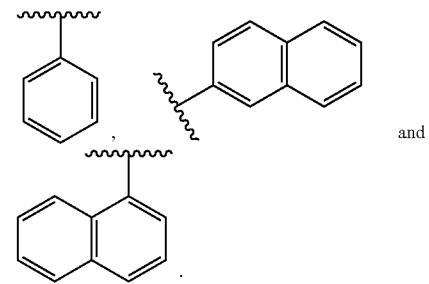

Examples of $C_{6-14}$-aryl are $C_{6-10}$-aryl and

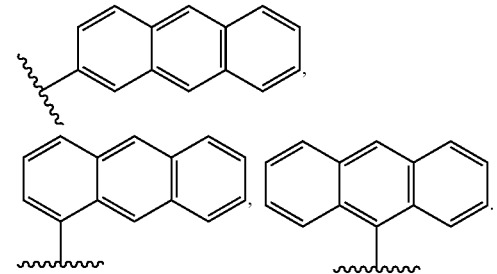

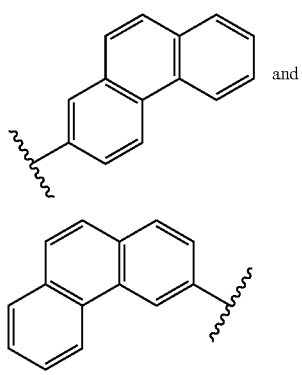
Examples of 5 to 9 membered heteroaryl are
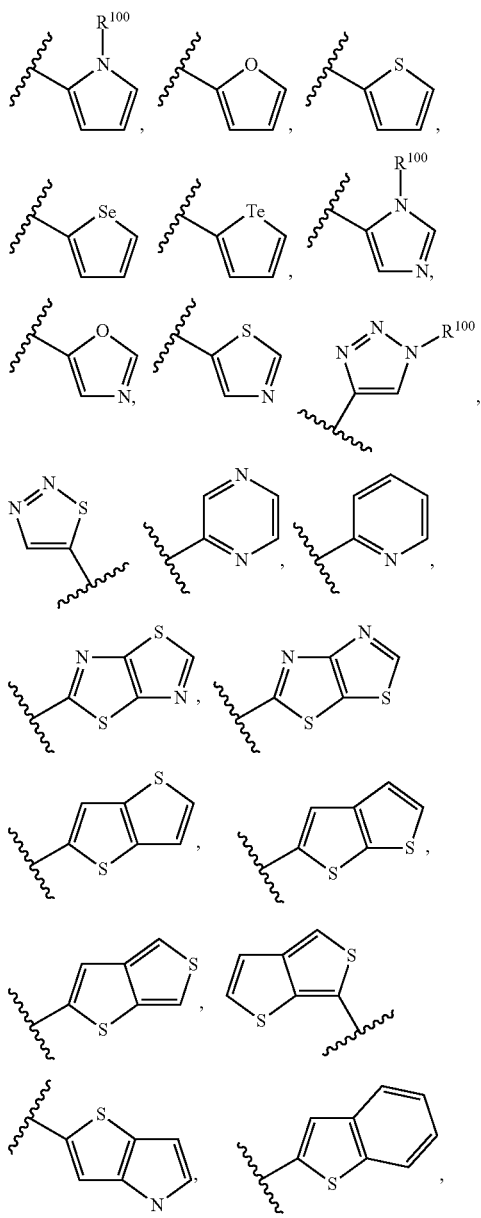
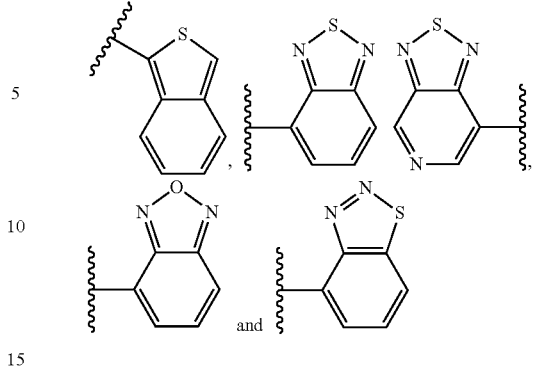
wherein $R^{100}$ is H or $C_{1-20}$-alkyl.
Examples of 5 to 12 membered heteroaryl are 5 to 9 membered heteroaryl and
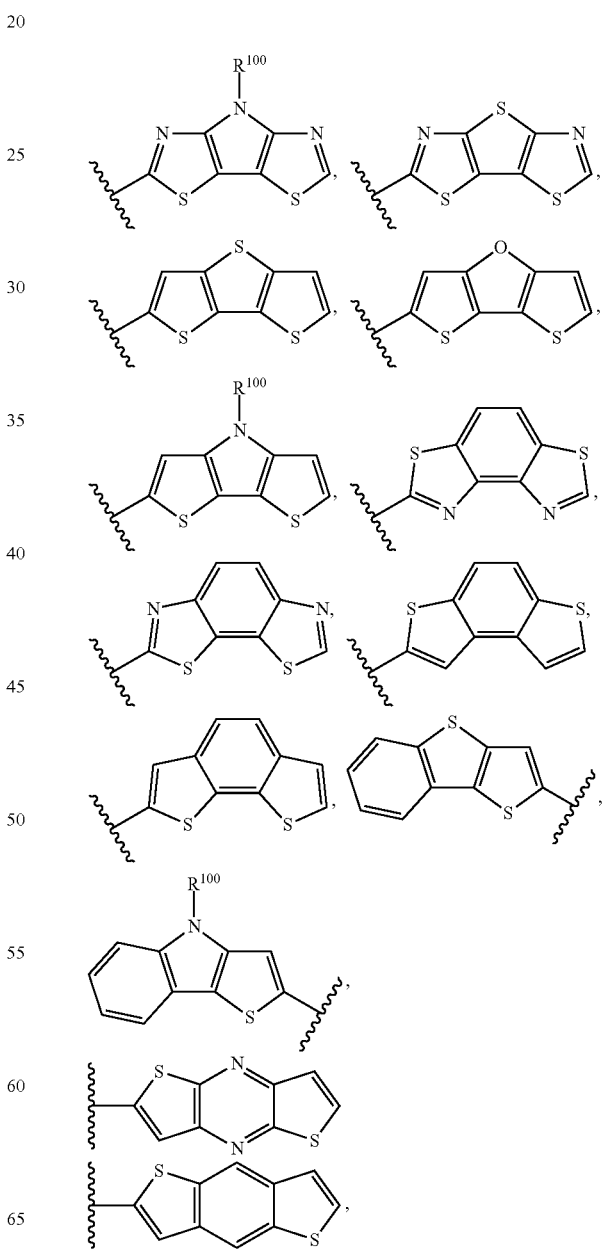

-continued

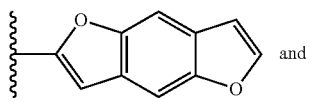
and

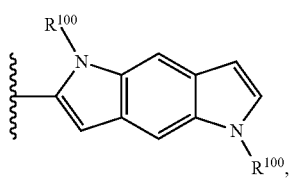

wherein R$^{100}$ is H or C$_{1-20}$-alkyl.

Examples of 5 to 15 membered heteroaryl are 5 to 12 membered heteroaryl and

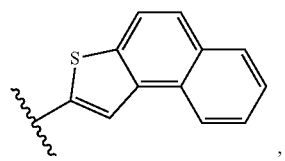,

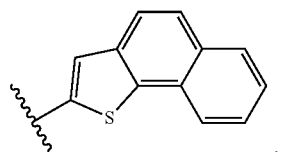,

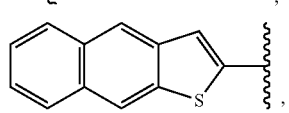,

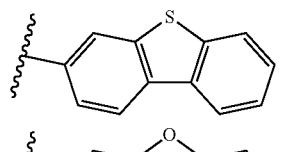,

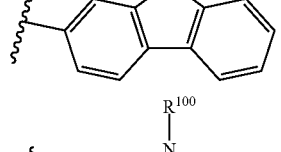,

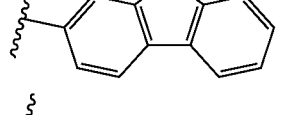,

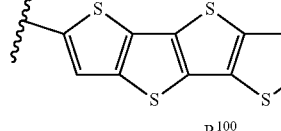,

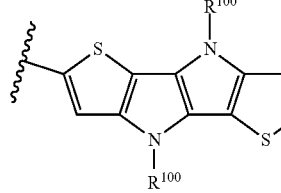,

-continued

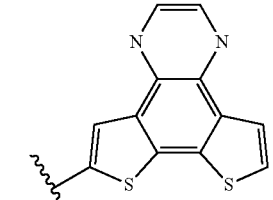
and

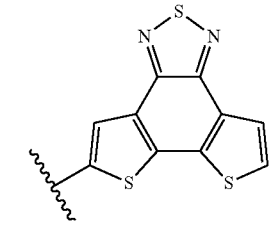, wherein R$^{100}$ is H or C$_{1-20}$-alkyl.

Examples of halogen are F, Cl, Br and I.

A 6 membered aromatic ring system is

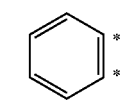

wherein the C-atoms marked with * are the C-atoms, to which R$^2$ and R$^3$, R$^3$ and R$^4$, R$^4$ and R$^5$, R$^6$ and R$^7$, R$^7$ and R$^8$, respectively, R$^8$ and R are connected.

Examples 6 to 10 membered aromatic ring system are

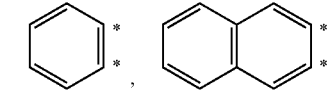
and

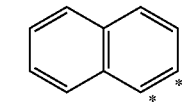

wherein the C-atoms marked with * are the C-atoms, to which R$^2$ and R$^3$, R$^3$ and R$^4$, R$^4$ and R$^5$, R$^6$ and R$^7$, R$^7$ and R$^8$, respectively, R$^8$ and R are connected.

Examples of 5 to 9 membered heteroaromatic ring system are

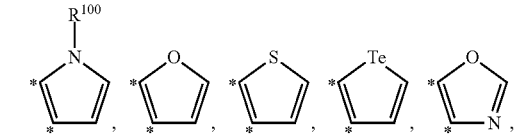

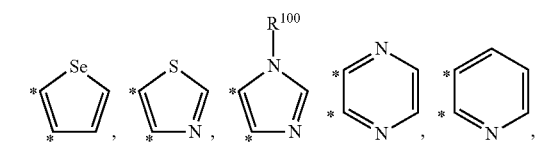,

-continued

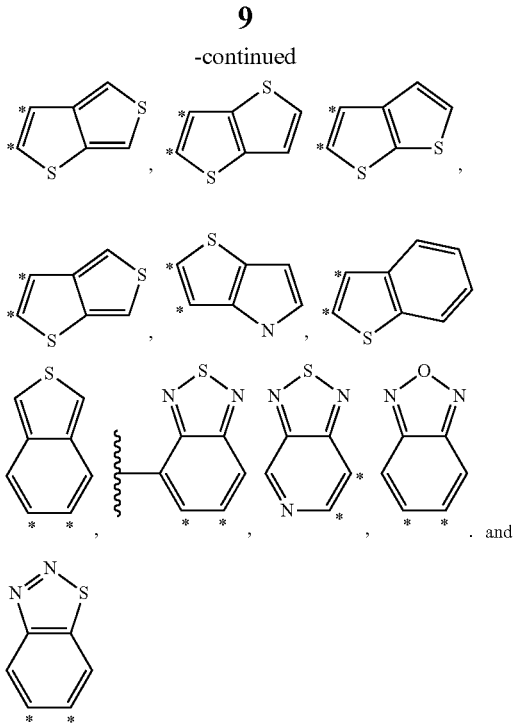

wherein R$^{100}$ is H or C$_{1-20}$-alkyl,
wherein the C-atoms marked with * are the C-atoms, to which R$^2$ and R$^3$, R$^3$ and R$^4$, R$^4$ and R$^5$, R$^6$ and R$^7$, R$^7$ and R$^8$, respectively, R$^8$ and R are connected.

Examples of 5 to 12 membered heteroaromatic ring system are 5 to 9 membered heteroaromatic ring systems and

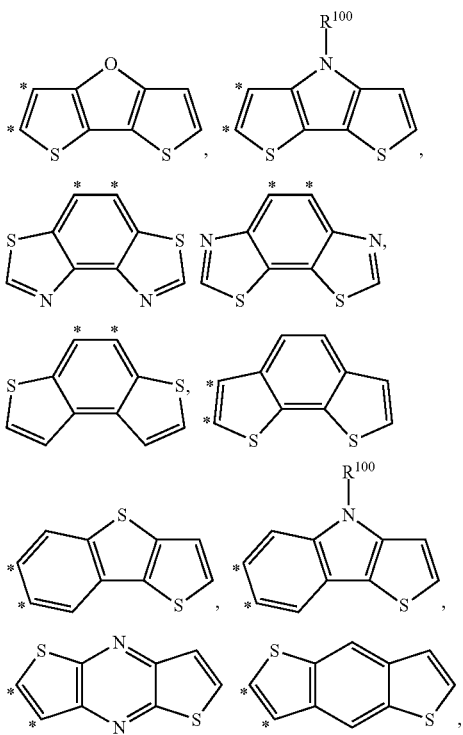

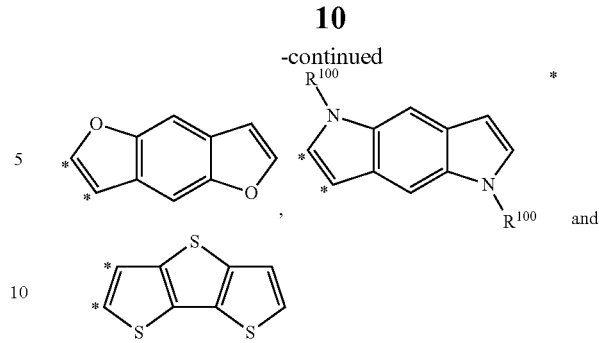

wherein R$^{100}$ is H or C$_{1-20}$-alkyl, and
wherein the C-atoms marked with * are the C-atoms, to which R$^2$ and R$^3$, R$^3$ and R$^4$, R$^4$ and R$^5$, R$^6$ and R$^7$, R$^7$ and R$^8$, respectively, R$^8$ and R are connected.

In preferred compounds of formula (1)
X is O, S or NR$^{10}$,
  wherein R$^{10}$ is H, C$_{1-30}$-alkyl, substituted C$_{1-30}$-alkyl, C$_{2-30}$-alkenyl, substituted C$_{2-30}$-alkenyl or C(O)—OR$^{11}$,
R$^1$ and R$^{11}$ are independently from each other selected from the group consisting of C$_{1-30}$-alkyl, substituted C$_{1-30}$-alkyl, C$_{2-30}$-alkenyl, substituted C$_{2-30}$-alkenyl, C$_{5-8}$-cycloalkyl, substituted C$_{5-8}$-cycloalkyl, C$_{5-8}$-cycloalkenyl and substituted C$_{5-8}$-cycloalkenyl,
R$^2$, R$^3$, R$^4$, R$^5$, R$^6$, R$^7$, R$^8$ and R$^9$ are independently from each other selected from the group consisting of H, C$_{1-30}$-alkyl, substituted C$_{1-30}$-alkyl, C$_{2-30}$-alkenyl, substituted C$_{2-30}$-alkenyl, C$_{5-8}$-cycloalkyl, substituted C$_{5-8}$-cycloalkyl, C$_{5-8}$-cycloalkenyl and substituted C$_{5-8}$-cycloalkenyl, O—C$_{1-30}$-alkyl, substituted O—C$_{1-30}$-alkyl, S—C$_{1-30}$-alkyl, substituted S—C$_{1-30}$-alkyl, C$_{6-14}$-aryl, substituted C$_{6-14}$-aryl, 5 to 15 membered heteroaryl, substituted 5 to 15 membered heteroaryl and halogen; or R$^2$ and R$^3$, R$^3$ and R$^4$, R$^4$ and R$^5$, R$^6$ and R$^7$, R$^7$ and R$^8$, or, R$^8$ and R$^9$ together with the C-atoms, to which they are connected, form a 6 to 10 membered aromatic ring system, substituted 6 to 10 membered aromatic ring system, 5 to 12 membered heteroaromatic ring system or a substituted 5 to 12 membered heteroaromatic ring system,
  wherein
  substituted C$_{1-30}$-alkyl, substituted C$_{2-30}$-alkenyl, substituted O—C$_{1-30}$-alkyl and substituted S—C$_{1-30}$-alkyl, at each occurrence, are C$_{1-30}$-alkyl, C$_{2-30}$-alkenyl, O—C$_{1-30}$-alkyl, respectively, S—C$_{1-30}$-alkyl, which are substituted with at least one substituent independently selected from the group consisting of C$_{5-6}$-cycloalkyl, C$_{6-10}$-aryl, 5 to 12 membered heteroaryl, OR$^a$, OC(O)—R$^a$, OC(O)—OR$^a$, OC(O)—NR$^a$R$^b$, C(O)—R$^a$, C(O)—OR$^a$, C(O)—NR$^a$R$^b$, C(O)—NR$^a$NR$^b$R$^c$, C(O)—NR$^a$—OR$^b$, C(O)—NR$^a$—C(O)—R$^b$, C(O)—NR$^a$—C(O)—OR$^b$, C(O)—SR$^a$, NR$^a$R$^b$, NR$^a$NR$^b$R$^c$, NR$^a$—C(O)R$^b$, NR$^a$—C(O)—OR$^b$, NR$^a$—C(O)—NR$^b$R$^c$, SR$^a$, S—C(O)—R$^a$, halogen, CN, and NO$_2$;
  substituted C$_{5-8}$-cycloalkyl and substituted C$_{5-8}$-cycloalkenyl, at each occurrence, are C$_{5-8}$-cycloalkyl, respectively, C$_{5-8}$-cycloalkenyl, which are substituted with at least one substituent independently selected from the group consisting of C$_{1-20}$-alkyl, C$_{5-6}$-cycloalkyl, C$_{6-10}$-aryl, 5 to 12 membered heteroaryl, OR$^a$, OC(O)—R$^a$, OC(O)—OR$^a$, OC(O)—NR$^a$R$^b$, C(O)—R$^a$, C(O)—OR$^a$, C(O)—NR$^a$R$^b$, C(O)—NR$^a$—NR$^b$R$^c$, C(O)—NR$^a$—OR$^b$, C(O)—NR$^a$—C(O)—R$^b$, C(O)—NR$^a$—C(O)—OR$^b$, C(O)—SR$^a$, NR$^a$R$^b$, NR$^a$—NR$^b$R$^c$, NR$^a$—C(O)R$^b$, NR$^a$—C(O)—OR$^b$, NR$^a$C(O)—NR$^b$R$^c$, SR$^a$, S—C(O)—R$^a$, halogen, CN, and NO$_2$; substituted C$_{6-14}$-aryl, substituted 5 to 15 membered heteroaryl, substituted 6 to 10 membered aromatic ring system and substituted 5 to 12 membered heteroaromatic ring system, at each occurrence, are C$_{6-14}$-aryl, 5 to 15 membered heteroaryl, 6 to 10 membered aromatic ring system, respectively, 5 to 12 membered heteroaromatic ring system, which are substituted with at least one substituent independently selected from the group consisting of C$_{1-20}$-alkyl, C$_{5-6}$-cycloalkyl, C$_{6-10}$-aryl, 5 to 12 membered heteroaryl, OR$^a$, OC(O)—R$^a$, OC(O)—OR$^a$, OC(O)—NR$^a$R$^b$, C(O)—R$^a$, C(O)—OR$^a$, C(O)—NR$^a$R$^b$, C(O)—NR$^a$—NR$^b$R$^c$, C(O)NR$^a$—OR$^b$, C(O)—NR$^a$—C(O)—R$^b$, C(O)—NR$^a$—C(O)—OR$^b$, C(O)—SR$^a$, NR$^a$R$^b$, NR$^a$—NR$^b$R$^c$, NR$^a$C(O)—R$^b$, NR$^a$—C(O)—OR$^b$, NR$^a$—C(O)—NR$^b$R$^c$, SR$^a$, S—C(O)—R$^a$, halogen, CN, and NO$_2$, wherein at least one CH$_2$-group, but not adjacent CH$_2$-groups, of C$_{1-30}$-alkyl, substituted C$_{1-30}$-alkyl, C$_{2-30}$-alkenyl, substituted C$_{2-30}$-alkenyl, C$_{5-8}$-cycloalkyl, substituted C$_{5-8}$-cycloalkyl, C$_{5-8}$-cycloalkenyl and substituted C$_{5-8}$-cycloalkenyl, O—C$_{1-30}$-alkyl, substituted O—C$_{1-30}$-alkyl, S—C$_{1-30}$-alkyl and substituted S—C$_{1-30}$-alkyl, can be replaced by a linking group selected from the group consisting of O, S, NR$^{12}$, CO, O—C(O), C(O)—O, O—C(O)—O, S—C(O), C(O)—S, NR$^{12}$—C(O), C(O)—NR$^{12}$, OC(O)—NR$^{12}$ and NR$^{12}$—C(O)—O, wherein R$^{12}$ is H, C$_{1-30}$-alkyl, substituted C$_{1-30}$-alkyl, or C(O)—OR$^d$, R$^a$, R$^b$, R$^c$ and R$^d$ are independently from each other and at each occurrence selected from the group consisting of H, C$_{1-20}$-alkyl, C$_{5-6}$-cycloalkyl, C$_{6-10}$-aryl, and 5 to 12 membered heteroaryl.

In more preferred compounds of formula (1)

X is O, S or NR$^{10}$, wherein R$^{10}$ is H, C$_{1-30}$-alkyl, substituted C$_{1-30}$-alkyl or C(O)—OR$^{11}$, R$^1$ and R$^{11}$ are independently from each other selected from the group consisting of C$_{1-30}$-alkyl, substituted C$_{1-30}$-alkyl, C$_{2-30}$-alkenyl, substituted C$_{2-30}$-alkenyl, C$_{5-8}$-cycloalkyl, substituted C$_{5-8}$-cycloalkyl, C$_{5-8}$-cycloalkenyl and substituted C$_{5-8}$-cycloalkenyl, R$^2$, R$^3$, R$^4$, R$^5$, R$^6$, R$^7$, R$^8$ and R$^9$ are independently from each other selected from the group consisting of H, C$_{1-30}$-alkyl, substituted C$_{1-30}$-alkyl, C$_{5-8}$-cycloalkyl, substituted C$_{5-8}$-cycloalkyl, C$_{6-14}$-aryl, substituted C$_{6-14}$-aryl, 5 to 15 membered heteroaryl and substituted 5 to 15 membered heteroaryl; or R$^2$ and R$^3$, R$^3$ and R$^4$, R$^4$ and R$^5$, R$^6$ and R$^7$, R$^7$ and R$^8$, or, R$^8$ and R$^9$ together with the C-atoms, to which they are connected, form a 6 to 10 membered aromatic ring system, substituted 6 to 10 membered aromatic ring system, 5 to 12 membered heteroaromatic ring system or a substituted 5 to 12 membered heteroaromatic ring system, wherein substituted C$_{1-30}$-alkyl and substituted C$_{2-30}$-alkenyl, at each occurrence, are C$_{1-30}$-alkyl, respectively, C$_{2-30}$-alkenyl, which are substituted with at least one substituent independently selected from the group consisting of C$_{5-6}$-cycloalkyl, C$_{6-10}$-aryl, 5 to 12 membered heteroaryl, OR$^a$, OC(O)—R$^a$, OC(O)—OR$^a$, OC(O)—NR$^a$R$^b$, C(O)—R$^a$, C(O)—OR$^a$, C(O)—NR$^a$R$^b$, C(O)—NR$^a$—NR$^b$R$^c$, C(O)—NR$^a$—OR$^b$, C(O)—NR$^a$—C(O)—R$^b$, C(O)—NR$^a$—C(O)—OR$^b$, C(O)—SR$^a$, NR$^a$R$^b$, NR$^a$—NR$^b$R$^c$, NR$^a$—C(O)R$^b$, NR$^a$—C(O)—OR$^b$, NR$^a$—C(O)—NR$^b$R$^c$, SR$^a$, S—C(O)—R$^a$, halogen, CN, and NO$_2$;

substituted C$_{5-8}$-cycloalkyl and substituted C$_{5-8}$-cycloalkenyl, at each occurrence, are C$_{5-8}$-cycloalkyl, respectively, C$_{5-8}$-cycloalkenyl, which are substituted with at least one substituent independently selected from the group consisting of C$_{1-20}$-alkyl, C$_{5-6}$-cycloalkyl, C$_{6-10}$-aryl, 5 to 12 membered heteroaryl, OR$^a$, OC(O)—R$^a$, OC(O)—OR$^a$, OC(O)—NR$^a$R$^b$, C(O)—R$^a$, C(O)—OR$^a$, C(O)—NR$^a$R$^b$, C(O)—NR$^a$—NR$^b$R$^c$, C(O)—NR$^a$—OR$^b$, C(O)—NR$^a$—C(O)—R$^b$, C(O)—NR$^a$—C(O)—OR$^b$, C(O)—SR$^a$, NR$^a$R$^b$, NR$^a$—NR$^b$R$^c$, NR$^a$—C(O)R$^b$, NR$^a$—C(O)—OR$^b$, NR$^a$C(O)—NR$^b$R$^c$, SR$^a$, S—C(O)—R$^a$, halogen, CN, and NO$_2$;

substituted C$_{6-14}$-aryl, substituted 5 to 15 membered heteroaryl, substituted 6 to 10 membered aromatic ring system, and substituted 5 to 12 membered heteroaromatic ring system, at each occurrence, are C$_{6-14}$-aryl, 5 to 15 membered heteroaryl, 6 to 10 membered aromatic ring system, respectively, 5 to 12 membered heteroaromatic ring system, which are substituted with at least one substituent independently selected from the group consisting of C$_{1-20}$-alkyl, C$_{5-6}$-cycloalkyl, C$_{6-10}$-aryl, 5 to 12 membered heteroaryl, OR$^a$, OC(O)—R$^a$, OC(O)—OR$^a$, OC(O)—NR$^a$R$^b$, C(O)—R$^a$, C(O)—OR$^a$, C(O)—NR$^a$R$^b$, C(O)—NR$^a$—NR$^b$R$^c$, C(O)NR$^a$—OR$^b$, C(O)—NR$^a$—C(O)—R$^b$, C(O)—NR$^a$—C(O)—OR$^b$, C(O)—SR$^a$, NR$^a$R$^b$, NR$^a$—NR$^b$R$^c$, NR$^a$C(O)—R$^b$, NR$^a$—C(O)—OR$^b$, NR$^a$—C(O)—NR$^b$R$^c$, SR$^a$, S—C(O)—R$^a$, halogen, CN, and NO$_2$, wherein at least one CH$_2$-group, but not adjacent CH$_2$-groups, of C$_{1-30}$-alkyl, substituted C$_{1-30}$-alkyl, C$_{2-30}$-alkenyl, substituted C$_{2-30}$-alkenyl, C$_{5-8}$-cycloalkyl, substituted C$_{5-8}$-cycloalkyl C$_{5-8}$-cycloalkenyl and substituted C$_{5-8}$-cycloalkenyl can be replaced by a linking group selected from the group consisting of O, S, NR$^{12}$, CO, O—C(O), C(O)—O, O—C(O)—O, S—C(O), C(O)—S, NR$^{12}$—C(O), C(O)—NR$^{12}$, OC(O)—NR$^{12}$ and NR$^{12}$—C(O)—O, wherein R$^{12}$ is H, C$_{1-30}$-alkyl, substituted C$_{1-30}$-alkyl or C(O)—OR$^d$, R$^a$, R$^b$, R$^c$ and R$^d$ are independently from each other and at each occurrence selected from the group consisting of H, C$_{1-20}$-alkyl, C$_{5-6}$-cycloalkyl, C$_{6-10}$-aryl, and 5 to 12 membered heteroaryl.

In even more preferred compounds of formula (1)

X is O, S or NR$^{10}$, wherein R$^{10}$ is H, C$_{1-30}$-alkyl, substituted C$_{1-30}$-alkyl or C(O)—OR$^{11}$, R$^1$ and R$^{11}$ are independently from each other selected from the group consisting of C$_{1-30}$-alkyl, substituted C$_{1-30}$-alkyl, C$_{2-30}$-alkenyl, substituted C$_{2-30}$-alkenyl, C$_{5-8}$-cycloalkyl, substituted C$_{5-8}$-cycloalkyl, C$_{5-8}$-cycloalkenyl and substituted C$_{5-8}$-cycloalkenyl, R$^2$, R$^3$, R$^4$, R$^5$, R$^6$, R$^7$, R$^8$ and R$^9$ are independently from each other selected from the group consisting of H, C$_{1-30}$-alkyl, substituted C$_{1-30}$-alkyl, C$_{5-8}$-cycloalkyl, substituted C$_{5-8}$-cycloalkyl, C$_{6-14}$-aryl, substituted C$_{6-14}$-aryl, 5 to 15 membered heteroaryl and substituted 5 to 15 membered heteroaryl; or R$^2$ and R$^3$, R$^3$ and R$^4$, R$^4$ and R$^5$, R$^6$ and R$^7$, R$^7$ and R$^8$, or, R$^8$ and R$^9$ together with the C-atoms, to which they are connected, form a 6 to 10 membered aromatic ring system, substituted 6 to 10 membered aromatic ring system, 5 to 12 membered heteroaromatic ring system or a substituted 5 to 12 membered heteroaromatic ring system, wherein substituted C$_{1-30}$-alkyl and substituted C$_{2-30}$-alkenyl, at each occurrence, are C$_{1-30}$-alkyl, respectively, C$_{2-30}$- alkenyl, which are substituted with at least one substituent independently selected from the group consisting of $C_{5-6}$-cycloalkyl, $C_{6-10}$-aryl, and 5 to 12 membered heteroaryl, substituted $C_{5-8}$-cycloalkyl and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{5-6}$-cycloalkyl, $C_{6-10}$-aryl, and 5 to 12 membered heteroaryl;

substituted $C_{6-14}$-aryl, substituted 5 to 15 membered heteroaryl, substituted 6 to 10 membered aromatic ring system, and substituted 5 to 12 membered heteroaromatic ring system, at each occurrence, are $C_{6-14}$-aryl, 5 to 15 membered heteroaryl, 6 to 10 membered aromatic ring system, respectively, 5 to 12 membered heteroaromatic ring system, which are substituted with at least one substituent independently selected from the group consisting of $C_{1-20}$-alkyl, $C_{5-6}$-cycloalkyl, $C_{6-10}$-aryl, 5 to 12 membered heteroaryl;

wherein at least one $CH_2$-group, but not adjacent $CH_2$-groups, of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl and substituted $C_{5-8}$-cycloalkenyl can be replaced by a linking group selected from the group consisting of O, S, and $NR^{12}$, wherein
$R^{12}$ is H, $C_{1-30}$-alkyl, substituted $C_{1-30}$-alkyl or $C(O)$—$OR^d$, $R^d$ is at each occurrence selected from the group consisting of H, $C_{1-20}$-alkyl, $C_{2-20}$-alkenyl, $C_{2-20}$-alkynyl, $C_{5-6}$-cycloalkyl, $C_{5-6}$-cycloalkenyl, $C_{6-10}$-aryl, and 5 to 12 membered heteroaryl.

In most preferred compounds of formula (1)
X is S,
$R^1$ is selected from the group consisting of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl and substituted $C_{5-8}$-cycloalkenyl,
$R^2$, $R^3$, $R^4$, $R^5$, $R^6$, $R^7$, $R^8$ and $R^9$ are independently from each other selected from the group consisting of H, $C_{1-30}$-alkyl, substituted $C_{1-30}$-alkyl, $C_{5-8}$-cycloalkyl, substituted $C_{5-8}$-cycloalkyl, $C_6$-10-aryl, substituted $C_{6-10}$-aryl, 5 to 12 membered heteroaryl, and substituted 5 to 12 membered heteroaryl; or $R^2$ and $R^3$, $R^3$ and $R^4$, $R^4$ and $R^5$, $R^6$ and $R^7$, $R^7$ and $R^8$, or, $R^8$ and $R^9$ together with the C-atoms, to which they are connected, form a 6 membered aromatic ring system, substituted 6 membered aromatic ring system, 5 to 9 membered heteroaromatic ring system or a substituted 5 to 9 membered heteroaromatic ring system,
wherein
substituted $C_{1-30}$-alkyl and substituted $C_{2-30}$-alkenyl, at each occurrence, are $C_{1-30}$-alkyl, respectively, $C_{2-30}$-alkenyl, which are substituted with at least one substituent independently selected from the group consisting of $C_{5-6}$-cycloalkyl, phenyl and 5 to 9 membered heteroaryl,
substituted $C_{5-8}$-cycloalkyl and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{5-6}$-cycloalkyl, phenyl and 5 to 9 membered heteroaryl, substituted $C_{6-10}$-aryl, substituted 5 to 12 membered heteroaryl, substituted 6 membered aromatic ring system, and substituted 5 to 9 membered heteroaromatic ring system, at each occurrence, are $C_{6-10}$-aryl, 5 to 12 membered heteroaryl, 6 membered aromatic ring system, respectively, 5 to 9 membered heteroaromatic ring system, which are substituted with at least one substituent independently selected from the group consisting of $C_{1-20}$-alkyl, $C_{5-6}$-cycloalkyl, phenyl, 5 to 9 membered heteroaryl, wherein at least one $CH_2$-group, but not adjacent $CH_2$-groups, of $C_{1-30}$-alkyl, substituted $C_{1-30}$-alkyl, $C_{5-8}$-cycloalkyl and substituted $C_{5-8}$-cycloalkyl, can be replaced by the linking group O.

In even most preferred compounds of formula (1)
X is S,
$R^1$ is selected from the group consisting of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl and substituted $C_{5-8}$-cycloalkenyl,
$R^2$, $R^3$, $R^4$, $R^5$, $R^6$, $R^7$, $R^8$ and $R^9$ are independently from each other selected from the group consisting of H, $C_{1-30}$-alkyl, substituted $C_{1-30}$-alkyl, $C_{5-8}$-cycloalkyl, and substituted $C_{5-8}$-cycloalkyl,
wherein
substituted $C_{1-30}$-alkyl and substituted $C_{2-30}$-alkenyl, at each occurrence, are $C_{1-30}$-alkyl, respectively, $C_{2-30}$-alkenyl, which are substituted with at least one substituent independently selected from the group consisting of $C_{5-6}$-cycloalkyl, phenyl and 5 to 9 membered heteroaryl,
substituted $C_{5-8}$-cycloalkyl and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{5-6}$-cycloalkyl, phenyl and 5 to 9 membered heteroaryl.

In particular preferred compounds of formula (1)
X is S,
$R^1$ is selected from the group consisting of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl and substituted $C_{5-8}$-cycloalkenyl,
$R^2$, $R^4$, $R^5$, $R^6$, $R^7$ and $R^9$ are H, and $R^3$ and $R^8$ are independently from each other selected from the group consisting of H, $C_{1-30}$-alkyl, substituted $C_{1-30}$-alkyl, $C_{5-8}$-cycloalkyl and substituted $C_{5-8}$-cycloalkyl,
wherein
substituted $C_{1-30}$-alkyl and substituted $C_{2-30}$-alkenyl, at each occurrence, are $C_{1-30}$-alkyl, respectively, $C_{2-30}$-alkenyl, which are substituted with at least one substituent independently selected from the group consisting of $C_{5-6}$-cycloalkyl and phenyl,
substituted $C_{5-8}$-cycloalkyl and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{5-6}$-cycloalkyl and phenyl.

Also part of the present invention is a process for the preparation of the compounds of formula

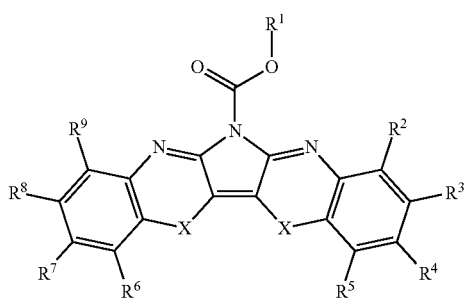

(1)

wherein
X is O, S or $NR^{10}$,
wherein $R^{10}$ is H, $C_{1-30}$-alkyl, substituted $C_{1-30}$-alkyl, $C_{2-30}$-alkenyl, substituted $C_{2-30}$-alkenyl, $C_{2-30}$-alkynyl, substituted $C_{2-30}$-alkynyl or $C(O)$—$OR^{11}$,
$R^1$ and $R^{11}$ are independently from each other selected from the group consisting of $C_{1-30}$-alkyl, substituted $C_{1-30}$-alkyl, $C_{2-30}$-alkenyl, substituted $C_{2-30}$-alkenyl, $C_{2-30}$-alkynyl, substituted $C_{2-30}$-alkynyl, $C_{5-8}$-cycloalkyl, substituted $C_{5-8}$-cycloalkyl, $C_{5-8}$-cycloalkenyl, and substituted $C_{5-8}$-cycloalkenyl,
$R^2$, $R^3$, $R^4$, $R^5$, $R^6$, $R^7$, $R^8$ and $R^9$ are independently from each other selected from the group consisting of H, $C_{1-30}$-alkyl, substituted $C_{1-30}$-alkyl, $C_{2-30}$-alkenyl, substituted $C_{2-30}$-alkenyl, $C_{2-30}$-alkynyl, substituted $C_{2-30}$-alkynyl, $C_{5-8}$-cycloalkyl, substituted $C_{5-8}$-cycloalkyl, $C_{5-8}$-cycloalkenyl, substituted $C_{5-8}$-cycloalkenyl, O—$C_{1-30}$-alkyl, substituted O—$C_{1-30}$-alkyl, S—$C_{1-30}$-alkyl, substituted S—$C_{1-30}$-alkyl, $C_{6-14}$-aryl, substituted $C_{6-14}$-aryl, 5 to 15 membered heteroaryl, substituted 5 to 15 membered heteroaryl and halogen; or $R^2$ and $R^3$, $R^3$ and $R^4$, $R^4$ and $R^5$, $R^6$ and $R^7$, $R^7$ and $R^8$, or, $R^8$ and $R^9$ together with the C-atoms, to which they are connected, form a 6 to 10 membered aromatic ring system, substituted 6 to 10 membered aromatic ring system, 5 to 12 membered heteroaromatic ring system or a substituted 5 to 12 membered heteroaromatic ring system,
wherein
substituted $C_{1-30}$-alkyl, substituted $C_{2-30}$-alkenyl, substituted $C_{2-30}$-alkynyl, substituted O—$C_{1-30}$-alkyl and substituted S—$C_{1-30}$-alkyl, at each occurrence, are $C_{1-30}$-alkyl, $C_{2-30}$-alkenyl, $C_{2-30}$-alkynyl, O—$C_{1-30}$-alkyl, respectively, S—$C_{1-30}$-alkyl, which are substituted with at least one substituent independently selected from the group consisting of $C_{5-6}$-cycloalkyl, $C_{6-10}$-aryl, 5 to 12 membered heteroaryl, $OR^a$, $OC(O)$—$R^a$, $OC(O)$—$OR^a$, $OC(O)$—$NR^aR^b$, $C(O)$—$R^a$, $C(O)$—$OR^a$, $C(O)$—$NR^aR^b$, $C(O)$—$NR^a$—$NR^bR^c$, $C(O)$—$NR^a$—$OR^b$, $C(O)$—$NR^a$—$C(O)$—$R^b$, $C(O)$—$NR^a$—$C(O)$—$OR^b$, $C(O)$—$SR^a$, $NR^aR^b$, $NR^a$—$NR^bR^c$, $NR^a$—$C(O)R^b$, $NR^a$—$C(O)$—$OR^b$, $NR^a$—$C(O)$—$NR^bR^c$, $SR^a$, S—$C(O)$—$R^a$, halogen, CN, and $NO_2$;
substituted $C_{5-8}$-cycloalkyl, and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{2-20}$-alkenyl, $C_{2-20}$-alkynyl, $C_{5-6}$-cycloalkyl, $C_{6-10}$-aryl, 5 to 12 membered heteroaryl, $OR^a$, $OC(O)$—$R^a$, $OC(O)$—$OR^a$, $OC(O)$—$NR^aR^b$, $C(O)$—$R^a$, $C(O)$—$OR^a$, $C(O)$—$NR^aR^b$, $C(O)$—$NR^a$—$NR^bR^c$, $C(O)$—$NR^a$—$OR^b$, $C(O)$—$NR^a$—$C(O)$—$R^b$, $C(O)$—$NR^a$—$C(O)$—$OR^b$, $C(O)$—$SR^a$, $NR^aR^b$, $NR^a$—$NR^bR^c$, $NR^a$—$C(O)$$R^b$, $NR^a$—$C(O)$—$OR^b$, $NR^a$—$C(O)$—$NR^bR^c$, $SR^a$, S—$C(O)$—$R^a$, halogen, CN, and $NO_2$;
substituted $C_{6-14}$-aryl, substituted 5 to 15 membered heteroaryl, substituted 6 to 10 membered aromatic ring system, and substituted 5 to 12 membered heteroaromatic ring system, at each occurrence, are $C_{6-14}$-aryl, 5 to 15 membered heteroaryl, 6 to 10 membered aromatic ring system, respectively, 5 to 12 membered heteroaromatic ring system, which are substituted with at least one substituent independently selected from the group consisting of $C_{1-20}$-alkyl, $C_{2-20}$-alkenyl, $C_{2-20}$-alkynyl, $C_{5-6}$-cycloalkyl, $C_{5-6}$-cycloalkenyl, $C_{6-10}$-aryl, 5 to 12 membered heteroaryl, $OR^a$, $OC(O)$—$R^a$, $OC(O)$—$OR^a$, $OC(O)$—$NR^aR^b$, $C(O)$—$R^a$, $C(O)$—$OR^a$, $C(O)$—$NR^aR^b$, $C(O)$—$NR^a$—$NR^bR^c$, $C(O)$—$NR^a$—$OR^b$, $C(O)$—$NR^a$—$C(O)$—$R^b$, $C(O)$—$NR^a$—$C(O)$—$OR^b$, $C(O)$—$SR^a$, $NR^aR^b$, $NR^a$—$NR^bR^c$, $NR^a$—$C(O)$$R^b$, $NR^a$—$C(O)$—$OR^b$, $NR^aC(O)$—$NR^bR^c$, $SR^a$, S—$C(O)$—$R^a$, halogen, CN, and $NO_2$,
wherein at least one $CH_2$-group, but not adjacent $CH_2$-groups, of $C_{1-30}$-alkyl, substituted $C_{1-30}$-alkyl, $C_{2-30}$-alkenyl, substituted $C_{2-30}$-alkenyl, $C_{2-30}$-alkynyl, substituted $C_{2-30}$-alkynyl, $C_{5-8}$-cycloalkyl, substituted $C_{5-8}$-cycloalkyl, $C_{5-8}$-cycloalkenyl, substituted $C_{5-8}$-cycloalkenyl, O—$C_{1-30}$-alkyl, substituted O—$C_{1-30}$-alkyl, S—$C_{1-30}$-alkyl and substituted S—$C_{1-30}$-alkyl, can be replaced by a linking group selected from the group consisting of O, S, $NR^{12}$, CO, O—$C(O)$, $C(O)$—O, O—$C(O)$—O, S—$C(O)$, $C(O)$—S, $NR^{12}$—$C(O)$, $C(O)$—$NR^{12}$, $OC(O)$—$NR^{12}$ and $NR^{12}$—$C(O)$—O,
wherein
$R^{12}$ is H, $C_{1-30}$-alkyl, substituted $C_{1-30}$-alkyl, $C_{2-30}$-alkenyl, substituted $C_{2-30}$-alkenyl, $C_{2-30}$-alkynyl, substituted $C_{2-30}$-alkynyl or $C(O)$—$OR^d$,
$R^a$, $R^b$, $R^c$ and $R^d$ are independently from each other and at each occurrence selected from the group consisting of H, $C_{1-20}$-alkyl, $C_{2-20}$-alkenyl, $C_{2-20}$-alkynyl, $C_{5-6}$-cycloalkyl, $C_{5-6}$-cycloalkenyl, $C_{6-10}$-aryl, and 5 to 12 membered heteroaryl,
which process comprises the step of treating a compound of formula

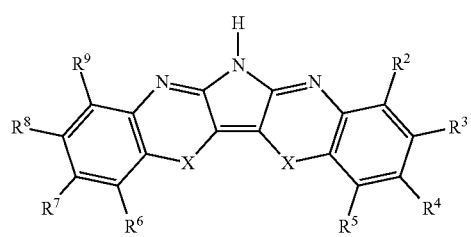

(2)

wherein X, $R^2$, $R^3$, $R^4$, $R^5$, $R^6$, $R^7$, $R^8$ and $R^9$ have the meaning as indicated for the compound of formula (1) with $R^1O$—$C(O)$-LG wherein $R^1$ has the meaning as indicated for the compound of formula (1), and LG is a leaving group
in order to obtain a compound of formula (1).

The leaving group LG can be —O—$C(O)$—$OR^1$, wherein $R^1$ has the meaning as indicated for the compound of formula (1), or

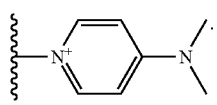

The reaction is usually performed at ambient temperatures. The reaction is usually performed in a suitable organic solvent such as THF.

If $R^2$, $R^3$, $R^4$, $R^5$, $R^6$, $R^7$, $R^8$ and $R^9$ are all H, and X is S, the compound of formula (2) has formula

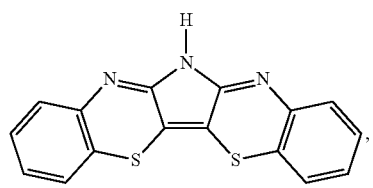

(2a)

and can be prepared by treating o-aminothiophenol with dichloromaleimide. The reaction is usually performed at elevated temperatures, such as at a temperature in the range of 80 to 150° C., and in the presence of acetic acid.

If X is S, the compound of formula (2) has formula

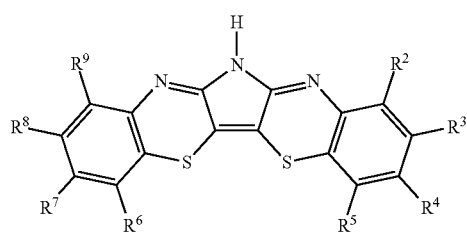

(2-I)

wherein
$R^2$, $R^3$, $R^4$, $R^5$, $R^6$, $R^7$, $R^8$ and $R^9$ have the meaning as indicated for the compound of formula (2),
and can be prepared by treating a compound of formula

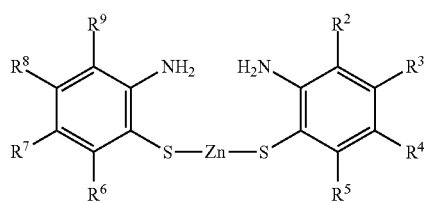

(3)

wherein $R^2$, $R^3$, $R^4$, $R^5$, $R^6$, $R^7$, $R^8$ and $R^9$ have the meaning as indicated for the compound of formula (2), with dichloromaleimide.

The reaction is usually performed at elevated temperatures, such as at a temperature in the range of 80 to 180° C., and in the presence of acetic acid.

If $R^9=R^2$, $R^8=R^3$, $R^7=R^4$ and $R^6=R^5$, the compound of formula (3) has formula

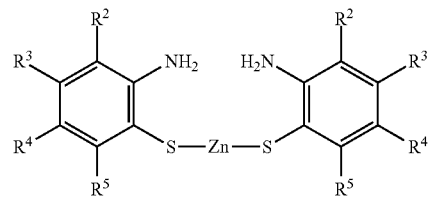

(3-I)

wherein $R^2$, $R^3$, $R^4$ and $R^5$ have the meaning as indicated for the compound of formula (2), and can be prepared by treating a compound of

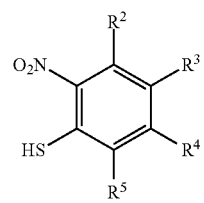

(4)

wherein $R^2$, $R^3$, $R^4$ and $R^5$ have the meaning as indicated for the compound of formula (2) with zinc.

The reaction is usually performed at elevated temperatures, such as at a temperature in the range of 40 to 80° C., and in the presence of an acid such as HCl or acetic acid.

A compound of formula

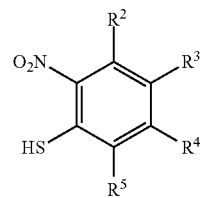

(4)

wherein $R^2$, $R^3$, $R^4$ and $R^5$ have the meaning as indicated for the compound of formula (2), can be prepared by heating a compound of formula

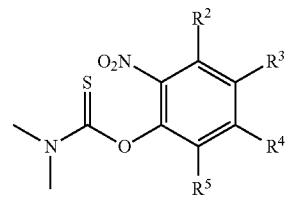

(5)

wherein $R^2$, $R^3$, $R^4$ and $R^5$ have the meaning as indicated for the compound of formula (2), The reaction is usually performed at elevated temperatures, such as at a temperature in the range of 160 to 260° C.

The compound of formula

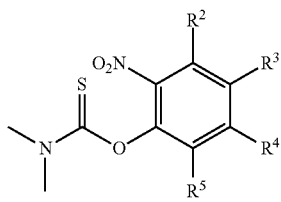

(5)

wherein $R^2$, $R^3$, $R^4$ and $R^5$ have the meaning as indicated for the compound of formula (2), can be prepared by treating a compound of formula

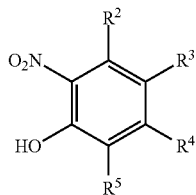

(6)

with N,N-dimethylthiocarbamoyl chloride.

The reaction is usually performed in the presence of a base. An examples of a base is 1,4-diazabicyclo[2.2.2]octane (DABCO). The reaction is usually performed at elevated temperatures, such as at a temperature in the range of 50 to 120° C. The reaction is usually performed in a suitable organic solvent such as DMF.

The compound of formula

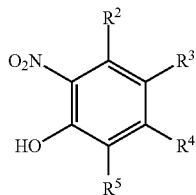

(6)

can be prepared by treating a compound of formula

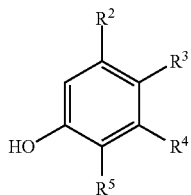

(7)

wherein $R^2$, $R^3$, $R^4$ and $R^5$ have the meaning as indicated for the compound of formula (2), nitric acid.

The reaction is usually performed at a temperature in the range of 10 to 20° C. The reaction is usually performed in the presence of an acid such as acetic acid.

Also part of the invention is an electronic device comprising the compounds of the present invention.

The electronic device can be an organic photovoltaic device (OPVs), an organic field-effect transistor (OFETs), an organic light emitting diode (OLEDs) or an organic photodiode (OPDs).

Preferably, the electronic device is an organic photovoltaic device (OPVs), an organic field-effect transistor (OFETs) or an organic photodiode (OPDs).

More preferably, the electronic device is an organic field effect transistor (OFET).

Usually, an organic field effect transistor comprises a dielectric layer, a semiconducting layer and a substrate. In addition, an organic field effect transistor usually comprises a gate electrode and source/drain electrodes.

Preferably, the semiconducting layer comprises the compounds of the present invention. The semiconducting layer can have a thickness of 5 to 500 nm, preferably of 10 to 100 nm, more preferably of 20 to 50 nm.

The dielectric layer comprises a dielectric material. The dielectric material can be silicon dioxide or aluminium oxide, or, an organic polymer such as polystyrene (PS), poly(methylmethacrylate) (PMMA), poly(4-vinylphenol) (PVP), poly(vinyl alcohol) (PVA), benzocyclobutene (BCB), or polyimide (PI). The dielectric layer can have a thickness of 10 to 2000 nm, preferably of 50 to 1000 nm, more preferably of 100 to 800 nm.

The dielectric layer can in addition to the dielectric material comprise a self-assembled monolayer of organic silane derivates or organic phosphoric acid derivatives. An example of an organic silane derivative is octyltrichlorosilane. An examples of an organic phosphoric acid derivative is decylphosphoric acid. The self-assembled monolayer comprised in the dielectric layer is usually in contact with the semiconducting layer.

The source/drain electrodes can be made from any suitable organic or inorganic source/drain material. Examples of inorganic source/drain materials are gold (Au), silver (Ag) or copper (Cu), as well as alloys comprising at least one of these metals. The source/drain electrodes can have a thickness of 1 to 100 nm, preferably from 20 to 70 nm.

The gate electrode can be made from any suitable gate material such as highly doped silicon, aluminium (Al), tungsten (W), indium tin oxide or gold (Au), or alloys comprising at least one of these metals. The gate electrode can have a thickness of 1 to 200 nm, preferably from 5 to 100 nm.

The substrate can be any suitable substrate such as glass, or a plastic substrate such as polyethersulfone, polycarbonate, polysulfone, polyethylene terephthalate (PET) and polyethylene naphthalate (PEN). Depending on the design of the organic field effect transistor, the gate electrode, for example highly doped silicon can also function as substrate.

The organic field effect transistor can be prepared by methods known in the art.

For example, a bottom-gate top-contact organic field effect transistor can be prepared as follows: The dielectric material, for example $Al_2O_3$ or silicon dioxide, can be applied as a layer on a gate electrode such as highly doped silicon wafer, which also functions as substrate, by a suitable deposition method such as atom layer deposition (ALD) or thermal evaporation. A self-assembled monolayer of an organic phosphoric acid derivative or an organic silane derivative can be applied to the layer of the dielectric material. For example, the organic phosphoric acid derivative or the organic silane derivative can be applied from solution using solution-deposition techniques. The semiconducting layer can be formed by either solution deposition or thermal evaporation in vacuo of the compounds of the present invention on the self-assembled monolayer of the organic phosphoric acid derivative or the organic silane derivative. Source/drain electrodes can be formed by deposition of a suitable source/drain material, for example tantalum (Ta) and/or gold (Au), on the semiconducting layer through a shadow masks. The channel width (W) is typically 500 μm and the channel length (L) is typically 100 μm.

For example, a top-gate bottom-contact organic field effect transistor can be prepared as follows: Source/drain electrodes can be formed by evaporating a suitable source/drain material, for example gold (Au), on photo-lithographically defined electrodes on a suitable substrate, for example a glass substrate. The semiconducting layer can be formed by depositing a solution of the compounds of the present invention, for example by spin-coating, on the source/drain electrodes, followed by annealing the layer at elevated temperatures such as at a temperature in the range of 80 to 360° C. After quenching the semiconducting layer, a dielectric layer can be formed by applying, for example, by spin-coating, a solution of a suitable dielectric material such as poly(methylmethacrylate), on the semiconducting layer. The gate electrode of a suitable source/drain material, for example gold (Au), can be evaporated through a shadow mask on the dielectric layer.

Also part of the invention is the use of the compounds of the present invention as semiconducting material.

The compounds of the present invention show high solubility in organic solvents, such as toluene, DMF, THF, chlorobenzene and $CHCl_3$, and are thus compatible with liquid processing techniques. At the same time, the compounds of the present invention, when applied as a layer in an organic electronic device, yield organic electronic devices showing good performance such as high charge carrier mobilities, preferably of above $5.0 \times 10^{-3}$ $cm^2$ $V^{-1}s^{-1}$.

In addition, the compounds of the present invention also show high stability towards oxidation by air.

Figure 9:
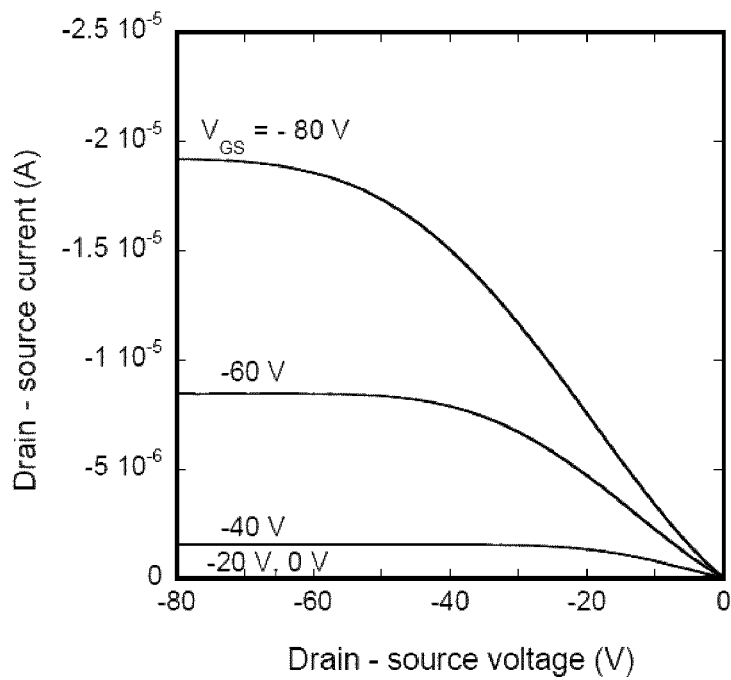

FIG. 9 shows the drain-source current $I_{DS}$ in relation to the drain-source voltage $V_{DS}$ (output curve) for the field effect transistor of example 16 comprising compound 1b as semiconducting material at a gate voltage $V_{GS}$ of −80 V, −60 V, −40 V, −20 V and 0 V.

Figure 10:
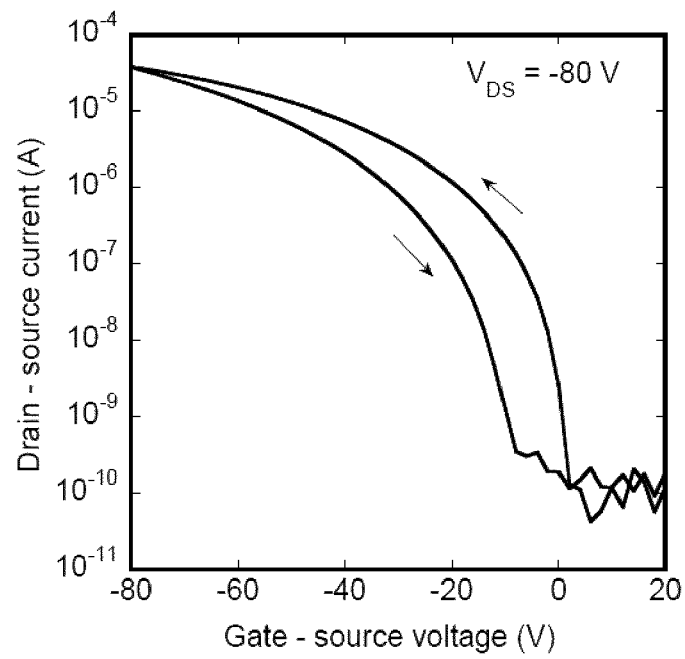

FIG. 10 shows the drain-source current $I_{DS}$ in relation to the gate-source voltage $V_{GS}$ (transfer curve) for field effect transistor of example 16 comprising compound 1b as semiconducting material at a drain-source voltage $V_{DS}$ of −80 V.

EXAMPLES

Example 1

Preparation of Compound 1a

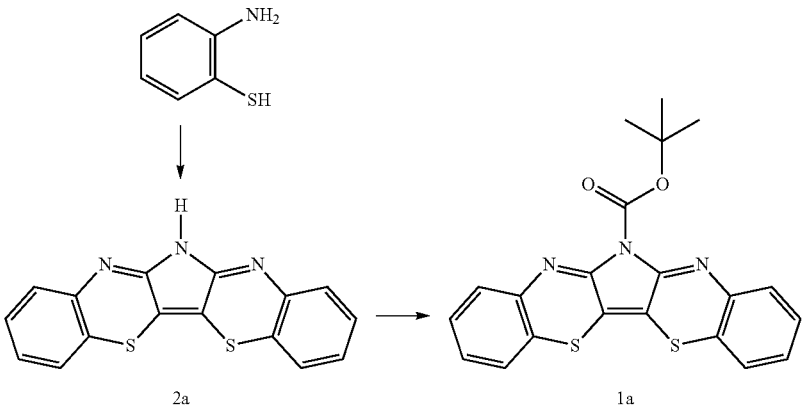 [SMILES: c1ccc2c(c1)N=c1[nH]c3c(c1S2)Sc1ccccc1N=3 ; Nc1ccccc1S ; CC(C)(C)OC(=O)n1c2c(c3c1=Nc1ccccc1S3)Sc1ccccc1N=2]

Preparation of Compound 2a 0.83 g (5 mmol) of dichloromaleimide and 1.25 g (10 mmol) of o-aminothiophenol were added to 30 ml of acetic acid, and stirred at 120° C. for 6 hours under $N_2$. After cooling to r.t., the precipitate was isolated by filtration, washed with methanol and THF. Compound 2a (1.26 g) was used in the next step without further purification.

Preparation of Compound 1a 215 mg (0.7 mmol) of compound 2a, 13 mg (0.1 mmol) of 4-dimethylaminopyridine, and 458 mg (2.1 mmol) of di-tert-butyl dicarbonate were added to 10 ml of THF, and stirred at r.t. overnight under $N_2$. The precipitate was isolated with filtration, washed with tert-butylmethylether, yielding 232 mg (0.57 mmol; 81%) of compound 1a as an orange solid. $^1$H-NMR spectrum (CDCl$_3$). δ [ppm] 1.72 (s, 9H), 7.15 (t, 2H), 7.21-7.28 (m, 4H), 7.50 (d, 2H).

Example 2

Preparation of Compound 1b

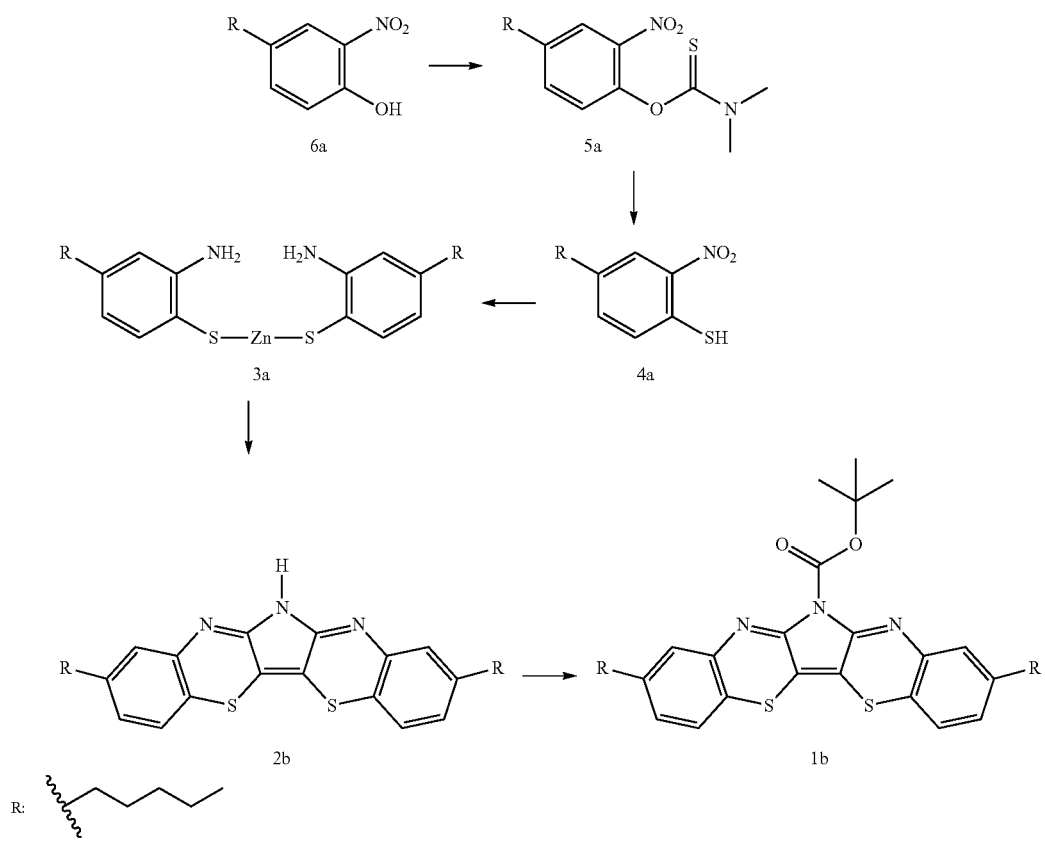

Preparation of Compound 6a

To a solution of 9.85 g (60 mmol) of 4-pentylphenol in 70 ml of acetic acid was added 7.6 g of nitric acid dissolved in 20 ml of acetic acid dropwise with keeping the temperature in the range of 10-15° C. The reaction mixture was stirred at r.t. for 4 hours, and then poured to water and extracted with ethyl acetate. The organic phase was washed with NaHCO$_3$aq and water, dried over MgSO$_4$, and concentrated. Compound 6a was used in the next step without further purification.

Preparation of Compound 5a

To a solution of 10.5 g (50 mmol) of compound 6a, 15.1 g (135 mmol) of DABCO in 50 ml of DMF was added 7.73 g (63 mmol) of N,N-dimethylthiocarbamoyl chloride by portions. The reaction mixture was stirred at 70° C. for 3 hours, and then poured to water and acidified with 6N HCl. Compound 5a was extracted with ethyl acetate, washed with water, dried over MgSO$_4$, and concentrated. The residue is purified by flash chromatography on silica gel with hexane and CH$_2$Cl$_2$ (1:1) as eluent, yielding 13.0 g (44 mmol; 88%) of compound 5a as a brown liquid. $^1$H-NMR (CDCl$_3$). δ [ppm]: 0.90 (t, 3H), 1.25-1.38 (m, 4H), 1.62-1.70 (m, 2H), 2.69 (t, 2H), 3.39 (s, 3H), 3.46 (s, 3H), 7.15 (d, 1H), 7.46 (d, 1H), 7.92 (s, 1H).

Preparation of Compound 4a 12.7 g (43 mmol) of compound 5a was placed in a reaction vessel and heated at 210° C. with stirred under $N_2$ for 3 hours. After cooling to r.t., 80 ml of THF was added. To the solution was added 5.31 g (95 mmol) of potassium hydroxide dissolved in 20 ml of methanol dropwise with cooled by an ice bath. The reaction mixture was stirred at r.t. for 30 min, and poured to ice, acidified with conc. HCl. Compound 4a was extracted with ethyl acetate, washed with water, dried over MgSO$_4$, and concentrated. $^1$H-NMR spectrum (CDCl$_3$). δ [ppm]: 0.89 (t, 3H), 1.25-1.37 (m, 4H), 1.55-1.65 (m, 2H), 2.63 (t, 2H), 3.96 (s, 1H), 7.25 (d, 1H), 7.33 (d, 1H), 8.06 (s, 1H).

Preparation of Compound 3a

To a solution of 5.15 g (23 mmol) of compound 4a in 9 ml of conc HCl and 170 ml of acetic acid was added 18.0 g (275 mmol) of zinc by portions at 60° C. The reaction mixture was stirred at 60° C. overnight. After cooling to r.t., insoluble solid was removed by filtration. The filtrate was concentrated by a rotary evaporator and water was added to the residue, yielding a precipitate.

The precipitate was isolated by filtration, washed with ethanol. Compound 3b was obtained with a yield of 5.16 g (11 mmol; 99%) as a white solid. $^1$H-NMR spectrum (DMSO-d$_6$). δ [ppm]: 0.83 (t, 6H), 1.18-1.32 (m, 8H), 1.42-1.53 (m, 4H), 2.39 (t, 4H), 5.72 (br s, 4H), 6.63 (d, 2H), 6.83 (s, 2H), 7.18 (d, 2H).

Preparation of Compound 2b

To 300 ml of acetic acid 7.26 g (16 mmol) of compound 3a and 2.66 g (16 mmol) of 3,4-dichloromaleimide were added and stirred at 140° C. overnight. After removing the solvent by a rotary evaporator, the residue was suspended in water. The solid was isolated by filtration, washed with methanol. Compound 2b was obtained as an orange solid. Compound 2b was used in the next step without further purification.

Preparation of Compound 1b

To 30 ml of THF 1.34 g (3 mmol) of compound 2b, 55 mg (0.45 mmol) of 4-dimethylaminopyridine, and 1.96 g (9 mmol) of di-tert-butyl dicarbonate were added, and stirred at r.t. overnight under $N_2$. The product was extracted with $CH_2Cl_2$, washed with water, dried over $MgSO_4$, and concentrated. The residue was purified by recrystallization from ethyl acetate and hexane (1:1) solution, yielding 1.06 g (1.9 mmol; 65%) of compound 1b as an orange solid. $^1$H-NMR ($CDCl_3$). δ [ppm]: 0.89 (t, 6H), 1.28-1.39 (m, 8H), 1.57-1.68 (m, 4H), 1.72 (s, 9H), 2.59 (t, 4H), 6.98 (d, 2H), 7.12 (d, 2H), 7.33 (s, 2H).

Example 3

Preparation of Compound 1c

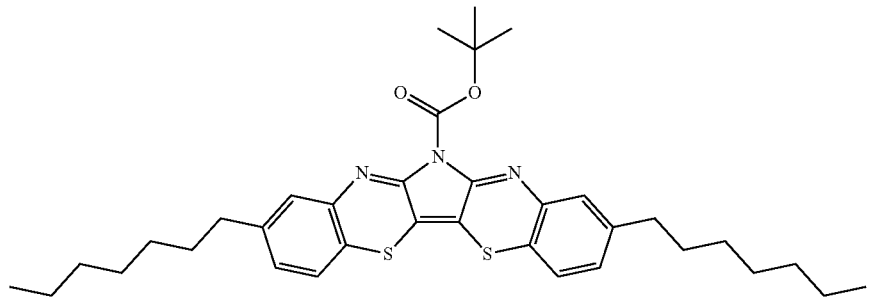

1c

Compound 1c is prepared in analogy to compound 1b in example 2, starting from 4-heptylphenol instead of from 4-pentylphenol, and is obtained as an orange solid. $^1$H-NMR spectrum ($CDCl_3$) δ [ppm]: 0.88 (t, 6H), 1.20-1.38 (m, 16H), 1.55-1.63 (m, 4H), 1.71 (s, 9H), 2.59 (t, 4H), 6.98 (d, 2H), 7.12 (d, 2H), 7.33 (s, 2H).

Example 4

Preparation of Compound 1d

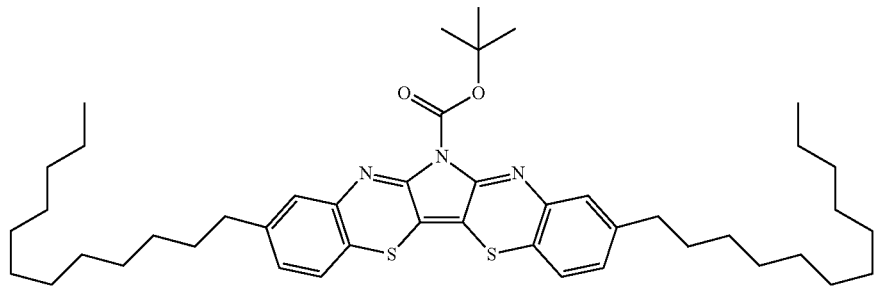

1d

Compound 1d is prepared in analogy to compound 1b in example 2, starting from 4-dodecylphenol instead of from 4-pentylphenol, and is obtained as an orange solid. $^1$H-NMR spectrum ($CDCl_3$) d [ppm]: 0.88 (t, 6H), 1.21-1.36 (m, 36H), 1.53-1.63 (m, 4H), 1.72 (s, 9H), 2.58 (t, 4H), 6.98 (d, 2H), 7.11 (d, 2H), 7.32 (s, 2H).

Example 5

Preparation of Compound

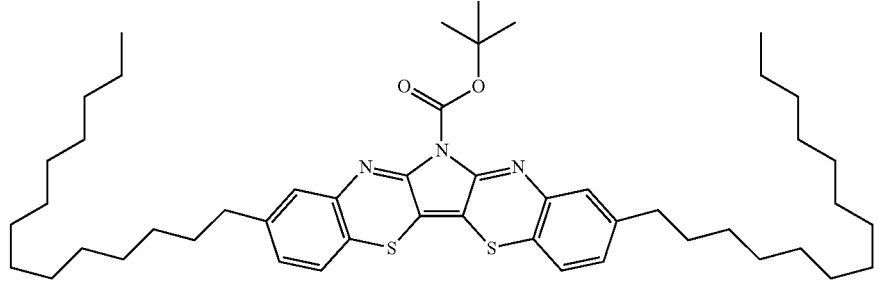

1e

Compound 1e is prepared in analogy to compound 1b in example 2, starting from 4-tetradecylphenol instead of from 4-pentylphenol, and is obtained as an orange solid. ¹H-NMR spectrum (CDCl₃) d [ppm]: 0.87 (t, 6H), 1.20-1.33 (m, 44H), 1.60-1.70 (m, 4H), 1.72 (s, 9H), 2.59 (t, 4H), 6.98 (d, 2H), 7.12 (d, 2H), 7.33 (s, 2H).

Example 6

Preparation of Compound 1f

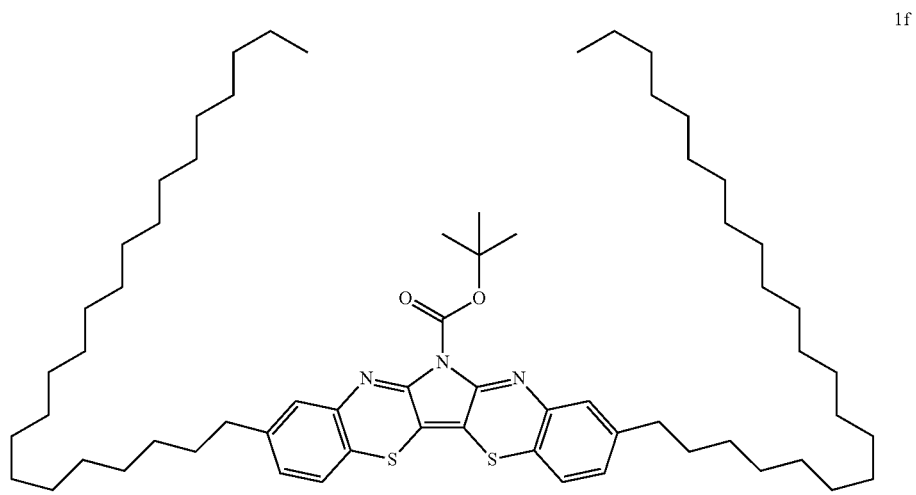 [SMILES: CCCCCCCCCCCCCCCCCCCCCCc1ccc2c(c1)N=c1c(c3c(n1C(=O)OC(C)(C)C)=Nc1cc(CCCCCCCCCCCCCCCCCCCCCC)ccc1S3)S2]

1f

Compound 1f is prepared in analogy to compound 1b in example 2, starting from 4-docosyl-phenol instead of from 4-pentylphenol, and is obtained as an orange solid. ¹H-NMR spectrum (CDCl₃) d [ppm]: 0.86 (t, 6H), 1.20-1.35 (m, 76H), 1.56-1.63 (m, 4H), 1.72 (s, 9H), 2.58 (t, 4H), 6.98 (d, 2H), 7.12 (d, 2H), 7.32 (s, 2H).

Example 7

Preparation of Compound 1g

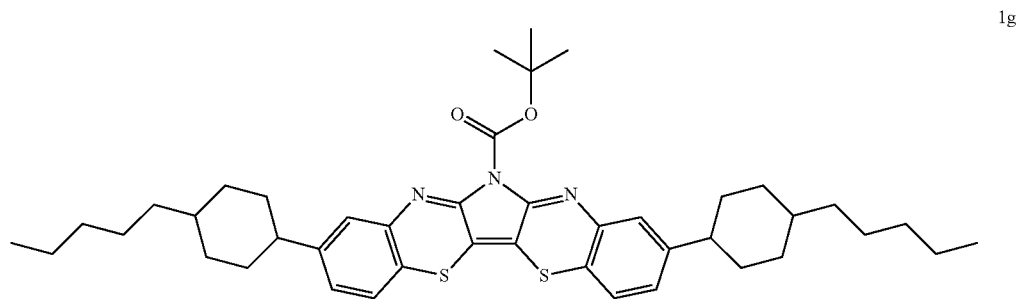 [SMILES: CCCCCC1CCC(c2ccc3c(c2)N=c2c(c4c(n2C(=O)OC(C)(C)C)=Nc2cc(C5CCC(CCCCC)CC5)ccc2S4)S3)CC1]

1g

Compound 1g is prepared in analogy to compound 1b in example 2, starting from 4-[4-pentylcyclohexyl)-phenol instead of from 4-pentylphenol, and is obtained as an orange solid. $^{1}$H-NMR spectrum (CDCl$_3$) d [ppm]: 0.89 (t, 6H), 0.98-1.10 (m, 4H), 1.18-1.38 (m, 18H), 1.38-1.52 (m, 4H), 1.72 (s, 9H), 1.83-1.92 (m, 8H), 2.40-2.49 (m, 2H), 7.02 (d, 2H), 7.12 (d, 2H), 7.35 (s, 2H).

Example 8

Preparation of Compound 1h

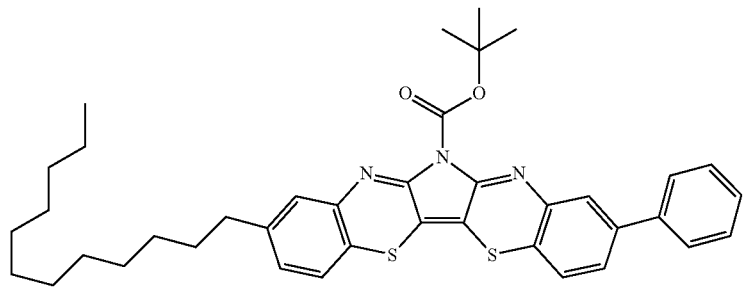

1h

Compound 1h is prepared in analogy to compound 1b in example 2, starting from 4-dodecylphenol instead of from 4-pentylphenol, and is obtained as an orange solid. $^{1}$H-NMR spectrum (CDCl$_3$) d [ppm]: 0.85 (t, 3H), 1.21-1.37 (m, 18H), 1.60-1.68 (m, 11H), 2.67 (t, 2H), 7.22 (d, 1H), 7.29 (d, 1H), 7.36-7.48 (m, 5H), 7.61-7.67 (m, 3H), 7.75 (s, 1H).

Example 9

Preparation of Compound 1i

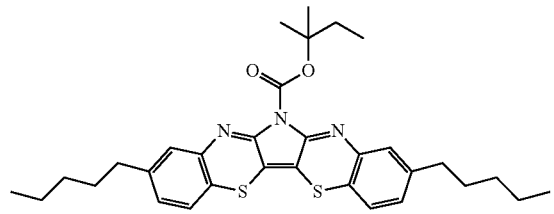

1i

Compound 1i is prepared in analogy to compound 1b in example 2, using di-(2-methyl-sec-butyl) dicarbonate instead of di-tert-butyl dicarbonate, and is obtained as an orange solid. $^{1}$H-NMR spectrum (CDCl$_3$) d [ppm]: 0.89 (t, 6H), 1.12 (t, 3H), 1.25-1.38 (m, 8H), 1.55-1.64 (m, 4H), 1.70 (s, 6H), 1.99 (q, 2H), 2.59 (t, 4H), 6.98 (d, 2H), 7.11 (d, 2H), 7.33 (s, 2H).

Example 10

Preparation of Compound 1j

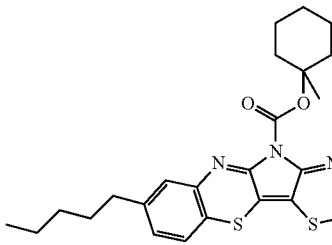

1j

Compound 1j is prepared in analogy to compound 1b in example 2, using di-(1-methylcyclohexyl) dicarbonate instead of di-tert-butyl dicarbonate, and is obtained as an orange solid. $^{1}$H-NMR spectrum (CDCl$_3$) d [ppm]: 0.80-0.95 (m, 6H), 1.10-1.65 (m, 21H), 1.95-2.08 (m, 2H), 2.40-2.49 (m, 2H), 2.58 (t, 4H), 6.98 (d, 2H), 7.12 (d, 2H), 7.34 (s, 2H).

Example 11

Preparation of Compound 1k

1k

Compound 1k is prepared in analogy to compound 1b in example 2, using di-(1-ethyl-1,5-dimethyl-hexyl) dicarbonate instead of di-tert-butyl dicarbonate, and is obtained as an orange solid. $^{1}$H-NMR spectrum (CDCl$_3$) d [ppm]: 0.86-0.91 (m, 12H), 1.07 (t, 3H), 1.20-1.37 (m, 12H), 1.47-1.67 (m, 8H), 1.85-2.13 (m, 4H), 2.58 (t, 4H), 6.97 (d, 2H), 7.11 (d, 2H), 7.32 (s, 2H).

Example 12

Preparation of Compound 11

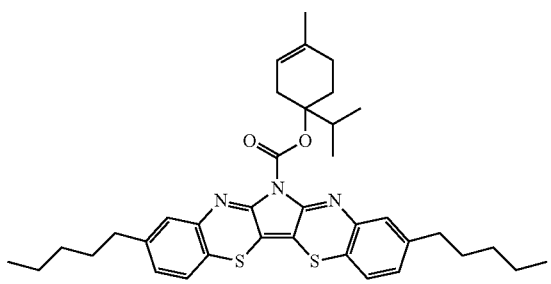

Compound 11 is prepared in analogy to compound 1b in example 2, using di-(1-isopropyl-4-methyl-cyclohex-3-en-1-yl) dicarbonate instead of di-tert-butyl dicarbonate, and is obtained as an orange solid. $^1$H-NMR spectrum (CDCl$_3$) d [ppm]: 0.80-1.72 (m, 27H), 1.75-1.87 (m, 1H), 1.92-2.03 (m, 1H), 2.27-2.45 (m, 2H), 2.58 (t, 4H), 2.65-2.79 (m, 1H), 2.92-3.02 (m, 1H), 5.32 (s, 1H), 6.97 (d, 2H), 7.12 (d, 2H), 7.29 (s, 2H).

Example 13

Preparation of Compound 1m

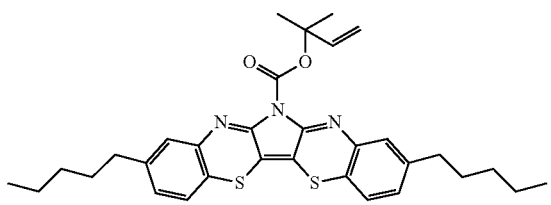

Compound 1m is prepared in analogy to compound 1b in example 2, using di-(1,1-dimethylallyl) dicarbonate instead of di-tert-butyl dicarbonate, and is obtained as an orange solid. $^1$H-NMR spectrum (CDCl$_3$) d [ppm]: 0.82-0.95 (m, 6H), 1.20-1.40 (m, 12H), 1.52-1.67 (m, 4H), 1.79 (s, 6H), 2.59 (t, 4H), 5.23 (d, 1H), 5.51 (d, 1H), 6.28 (dd, 1H), 6.98 (d, 2H), 7.11 (d, 2H), 7.33 (s, 2H).

Example 14

Preparation of Field-Effect Transistors Comprising Compounds 1a, 1b, 1e, Respectively, 1g as Semiconducting Material 30 nm ALD Al$_2$O$_3$ coated, highly doped silicon wafers were thoroughly cleaned with acetone and isopropanol and after a short oxygen plasma treatment treated with a solution of decyl-phosphonic acid in isopropanol. The compound 1a, 1b, 1e, respectively, 1g was thermally evaporated in high vacuum (<10$^{-5}$ mbar). A 50 nm-thick of Au layer for source and drain electrodes was deposited though a shadow mask to give top contact OFET devices. The channel width (W) was 500 μm and channel length (L) was 100 μm.

All electrical measurements were performed in ambient air in the dark using a B1500 Agilent parameter analyzer.

Figure 1:
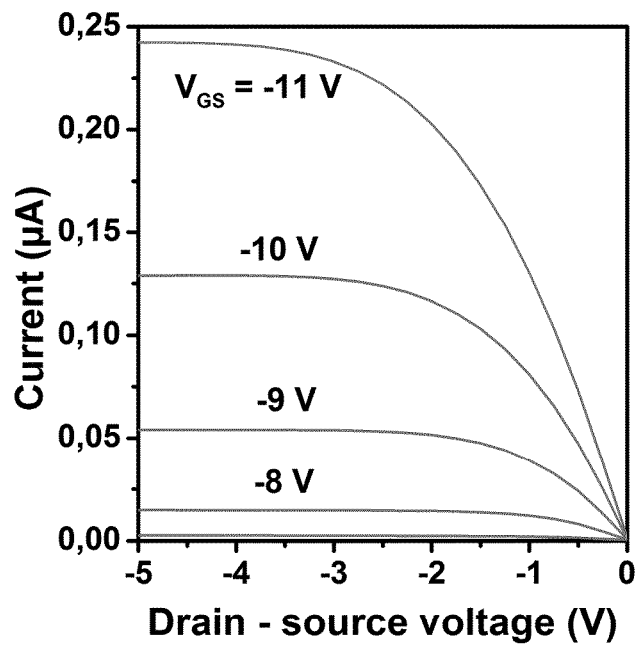
FIG. 1 shows the drain-source current $I_{ds}$ in relation to the drain-source voltage $V_{DS}$ (output curve) for the field effect transistor of example 14 comprising compound 1a as semiconducting material at a gate voltage $V_{GS}$ of −11 V, −10 V, −9 V and −8 V.

In FIG. 1 the drain-source current I$_{ds}$ in relation to the drain-source voltage V$_{DS}$ (output curve) for the field effect transistor of example 14 comprising compound 1a as semiconducting material at a gate voltage V$_{GS}$ Of −11 V, −10 V, −9 V and −8 V is shown.

Figure 2:
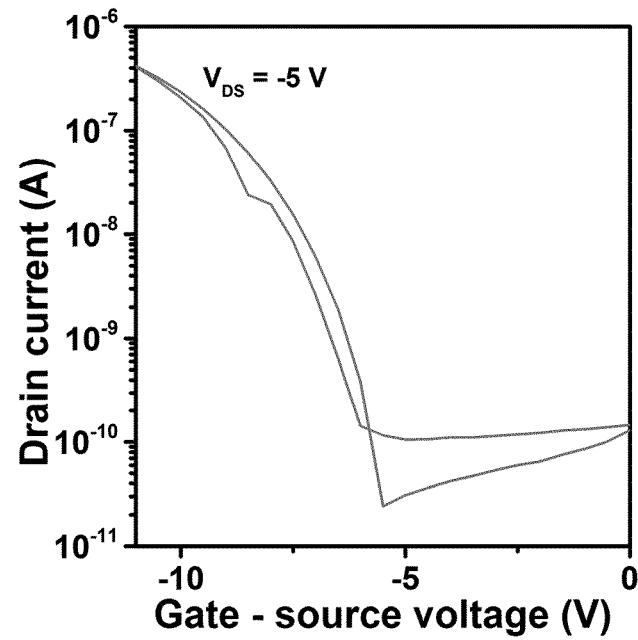
FIG. 2 shows the drain-source current $I_{DS}$ in relation to the gate-source voltage $V_{GS}$ (transfer curve) for field effect transistor of example 14 comprising compound 1a as semiconducting material at a drain-source voltage $V_{DS}$ of −5 V.

In FIG. 2 the drain-source current I$_{DS}$ in relation to the gate-source voltage V$_{GS}$ (transfer curve) for field effect transistor of example 14 comprising compound 1a as semiconducting material at a drain-source voltage V$_{DS}$ of −5 V is shown.

Figure 3:
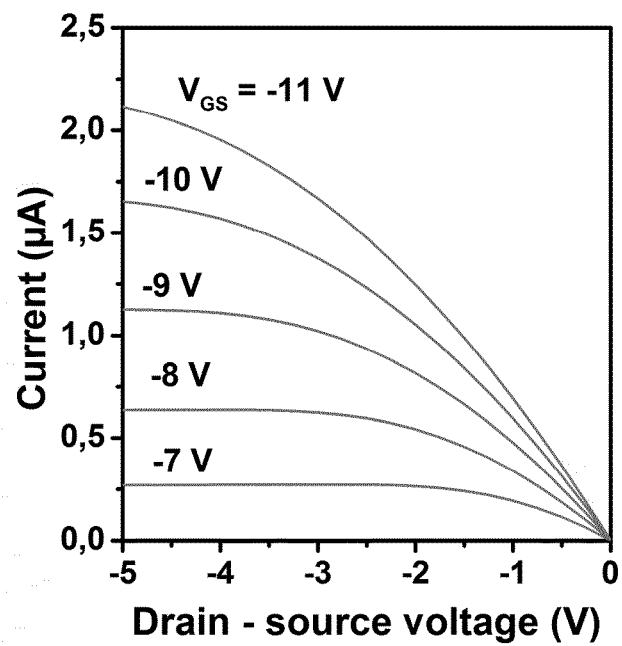
FIG. 3 shows the drain-source current $I_{ds}$ in relation to the drain-source voltage $V_{DS}$ (output curve) for the field effect transistor of example 14 comprising compound 1b as semiconducting material at a gate voltage $V_{GS}$ of −11 V, −10 V, −9 V and −7 V.

In FIG. 3 the drain-source current I$_{ds}$ in relation to the drain-source voltage V$_{DS}$ (output curve) for the field effect transistor of example 14 comprising compound 1b as semiconducting material at a gate voltage V$_{GS}$ Of −11 V, −10 V, −9 V and −7 V is shown.

Figure 4:
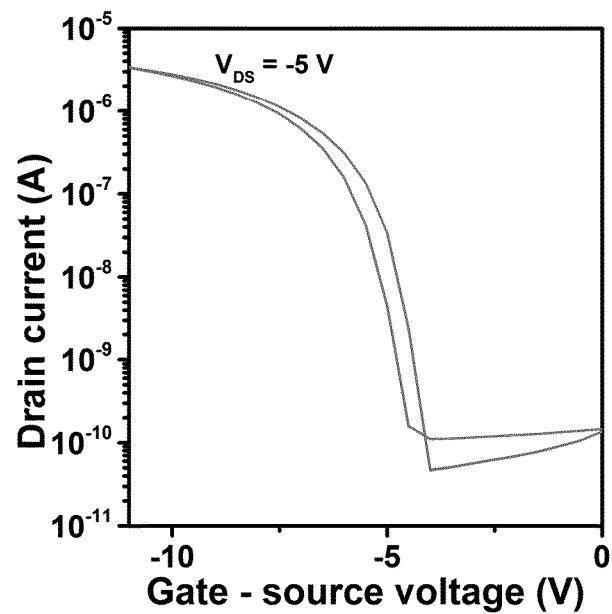
FIG. 4 shows the drain-source current $I_{DS}$ in relation to the gate-source voltage $V_{GS}$ (transfer curve) for field effect transistor of example 14 comprising compound 1b as semiconducting material at a drain-source voltage $V_{DS}$ of −5 V.

In FIG. 4 the drain-source current I$_{DS}$ in relation to the gate-source voltage V$_{GS}$ (transfer curve) for field effect transistor of example 14 comprising compound 1b as semiconducting material at a drain-source voltage V$_{DS}$ of −5 V is shown.

Figure 5:
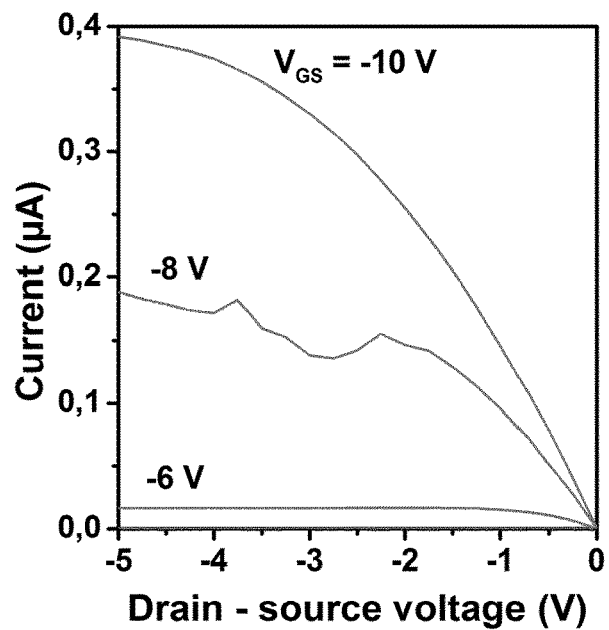
FIG. 5 shows the drain-source current $I_{ds}$ in relation to the drain-source voltage $V_{DS}$ (output curve) for the field effect transistor of example 14 comprising compound 1e as semiconducting material at a gate voltage $V_{GS}$ of −10 V, −8 V and −6 V.

In FIG. 5 the drain-source current I$_{ds}$ in relation to the drain-source voltage V$_{DS}$ (output curve) for the field effect transistor of example 14 comprising compound 1e as semiconducting material at a gate voltage V$_{GS}$ of −10 V, −8 V and −6 V is shown.

Figure 6:
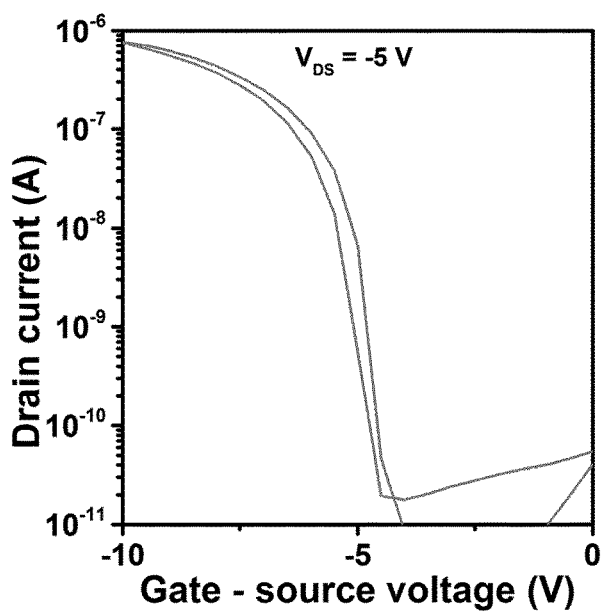
FIG. 6 shows the drain-source current $I_{DS}$ in relation to the gate-source voltage $V_{GS}$ (transfer curve) for field effect transistor of example 14 comprising compound 1e as semiconducting material at a drain-source voltage $V_{DS}$ of −5 V.

In FIG. 6 the drain-source current I$_{DS}$ in relation to the gate-source voltage V$_{GS}$ (transfer curve) for field effect transistor of example 14 comprising compound 1e as semiconducting material at a drain-source voltage V$_{DS}$ of −5 V is shown.

Figure 7:
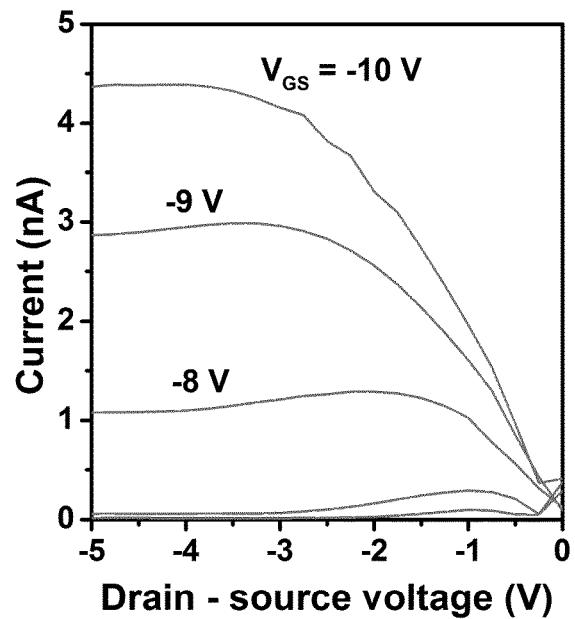
FIG. 7 shows the drain-source current $I_{ds}$ in relation to the drain-source voltage $V_{DS}$ (output curve) for the field effect transistor of example 14 comprising compound 1g as semiconducting material at a gate voltage $V_{GS}$ of −10 V, −9 V and −8 V.

In FIG. 7 the drain-source current I$_{ds}$ in relation to the drain-source voltage V$_{DS}$ (output curve) for the field effect transistor of example 14 comprising compound 1g as semiconducting material at a gate voltage V$_{GS}$ of −10 V, −9 V and −8 V is shown.

Figure 8:
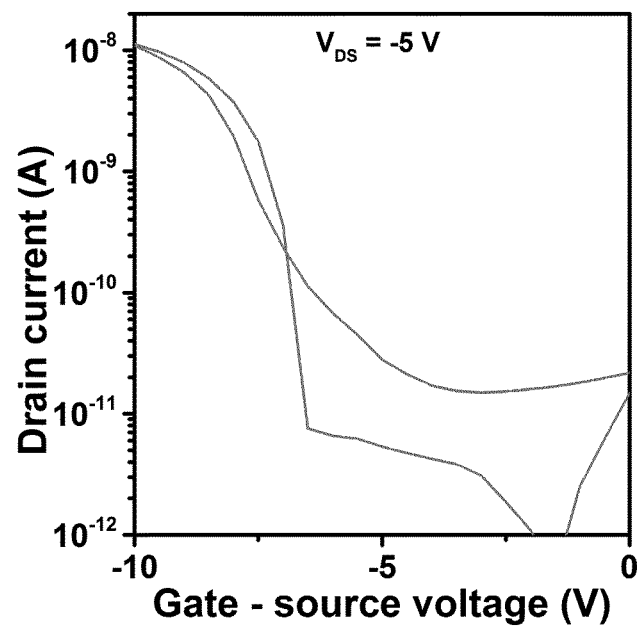
FIG. 8 shows the drain-source current $I_{DS}$ in relation to the gate-source voltage $V_{GS}$ (transfer curve) for field effect transistor of example 14 comprising compound 1g as semiconducting material at a drain-source voltage $V_{DS}$ of −5 V.

In FIG. 8 the drain-source current I$_{DS}$ in relation to the gate-source voltage V$_{GS}$ (transfer curve) for field effect transistor of example 14 comprising compound 1g as semiconducting material at a drain-source voltage V$_{DS}$ of −5 V is shown.

The field effect transistors comprising 1a, 1b, 1e, respectively, 1g showed typical p-type characteristics.

The charge-carrier mobility (μ) was extracted in the saturation regime from the slope of $(I_{DS})^{1/2}$ versus V$_{GS}$ using the equation $\mu=2L/(W*C_i)*(dI_{DS}^{1/2}/dV_{GS})^2$, wherein L is the channel length, W is the channel width, C$_i$ is the capacitance per unit area of the dielectric layer, I$_{DS}$ is the drain-source current, and V$_{GS}$ is the gate-source voltage.

The threshold voltage (V$_{th}$) was extracted from the intersection of the linear extrapolation of the I$_{DS}^{1/2}$ versus V$_{GS}$ plot with the V$_{GS}$ axis.

The results are depicted in table 1

TABLE 1

| Compound | V$_{th}$ [V] | μ [cm$^2$/Vs] | I$_{on/off}$ |
| --- | --- | --- | --- |
| 1a | −6.9 | 0.13 | 1E4 |
| 1b | −4.5 | 0.68 | 7E4 |
| 1e | −3.9 | 0.23 | 2E6 |
| 1g | −6.5 | 0.008 | 4E4 |

Example 15

The Solubility of the Compounds 1a, 1b, 1c and 1d at 25° C. were Compared to the Solubility of the Compound of Formula

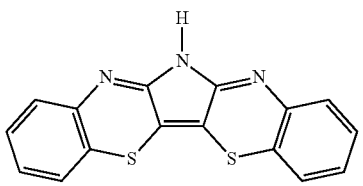

2a

The results are outlined in table 2

TABLE 2

| Compound | DMF | THF | clorobenzene | CHCl$_3$ |
|---|---|---|---|---|
| 2a (comparative) | <1 mg/mL | <1 mg/mL | <1 mg/mL | <1 mg/mL |
| 1a | 1 to 5 mg/mL | 1 to 5 mg/mL | 5 to 10 mg/mL | 5 to 10 mg/mL |
| 1b | <1 mg/mL | >10 mg/mL | >10 mg/mL | >10 mg/mL |
| 1c | <1 mg/mL | >10 mg/mL | >10 mg/mL | >10 mg/mL |
| 1d | >10 mg/mL | >10 mg/mL | >10 mg/mL | >10 mg/mL |

Example 16

Preparation of Field-Effect Transistors Comprising Compound 1b as Semiconducting Material SiO$_2$/Si substrates were thoroughly cleaned with piranha solution, ultrapure water, followed by isopropanol, and the substrates were functionalized with octadecyltrichlorosilane (OTS) from solution. A thin film of compound 1b was formed on the OTS-treated SiO$_2$/Si substrate by spin coating a 5 mg/ml solution of compound 1b in CHCl$_3$ at 4000 rpm for 30 sec, and annealed at 200° C. for 10 min on a hot-plate. On top of the organic thin film, Au layer was deposited through a shadow mask as source and drain electrodes to give top contact OFET devices. The channel width (W) was 3 mm and channel length (L) was 50 μm.

All electrical measurements are performed in ambient air in the dark using a Keithley 4200 parameter analyzer.

In FIG. 9 the drain-source current $I_{DS}$ in relation to the drain-source voltage $V_{DS}$ (output curve) for the field effect transistor of example 16 comprising compound 1b as semiconducting material at a gate voltage $V_{GS}$ of −80 V, −60 V, −40 V, −20 V and 0 V is shown.

In FIG. 10 the drain-source current $I_{DS}$ in relation to the gate-source voltage $V_{GS}$ (transfer curve) for field effect transistor of example 16 comprising compound 1b as semiconducting material at a drain-source voltage $V_{DS}$ of −80 V is shown.

The field effect transistors comprising 1b showed typical p-type characteristics.

To record the transfer curve the drain-source voltage ($V_{DS}$) was held to −80 V. The charge-carrier mobility (μ) was extracted in the saturation regime from the slope of $(I_{DS})^{1/2}$ versus $V_{GS}$ using the equation $\mu=2L/(W*C_i)*(dI_{DS}^{1/2}/dV_{GS})^2$, wherein L is the channel length, W is the channel width, $C_i$ is the capacitance per unit area of the dielectric layer, $I_{DS}$ is the drain-source current, and $V_{GS}$ is the gate-source voltage.

The threshold voltage ($V_{th}$) was extracted from the intersection of the linear extrapolation of the $I_{DS}^{1/2}$ versus $V_{GS}$ plot with the $V_{GS}$ axis.

The results are depicted in table 3

TABLE 3

| Compound | $V_{th}$/V | μ/cm$^2$/Vs | $I_{on/off}$ |
|---|---|---|---|
| Compound 1b | −9.0 | 0.022 | 3E5 |

The invention claimed is:

1. A compound of formula (1):

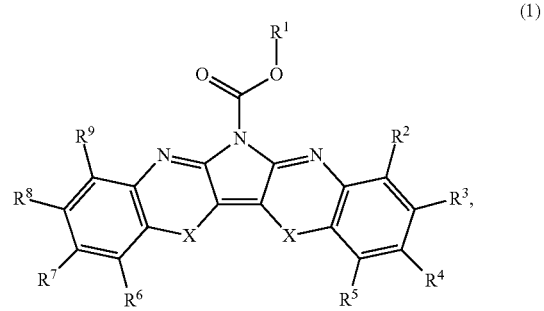

(1)

wherein:

X is O, S or NR$^{10}$,

R$^{10}$ is H, C$_{1-30}$-alkyl, substituted C$_{1-30}$-alkyl, C$_{2-30}$-alkenyl, substituted C$_{2-30}$-alkenyl, C$_{2-30}$-alkynyl, substituted C$_{2-30}$-alkynyl or C(O)—OR$^{11}$, R$^1$ and R$^{11}$ are independently from each other selected from the group consisting of C$_{1-30}$-alkyl, substituted C$_{1-30}$-alkyl, C$_{2-30}$-alkenyl, substituted C$_{2-30}$-alkenyl, C$_{2-30}$-alkynyl, substituted C$_{2-30}$-alkynyl, C$_{5-8}$-cycloalkyl, substituted C$_{5-8}$-cycloalkyl, C$_{5-8}$-cycloalkenyl, and substituted C$_{5-8}$-cycloalkenyl, R$^2$, R$^3$, R$^4$, R$^5$, R$^6$, R$^7$, R$^8$ and R$^9$ are independently from each other selected from the group consisting of H, C$_{1-30}$-alkyl, substituted C$_{1-30}$-alkyl, C$_{2-30}$-alkenyl, substituted C$_{2-30}$-alkenyl, C$_{2-30}$-alkynyl, substituted C$_{2-30}$-alkynyl, C$_{5-8}$-cycloalkyl, substituted C$_{5-8}$-cycloalkyl, C$_{5-8}$-cycloalkenyl, substituted C$_{5-8}$-cycloalkenyl, O—C$_{1-30}$-alkyl, substituted O—C$_{1-30}$-alkyl, S—C$_{1-30}$-alkyl, substituted S—C$_{1-30}$-alkyl, C$_{6-14}$-aryl, substituted C$_{6-14}$-aryl, 5 to 15 membered heteroaryl, substituted 5 to 15 membered heteroaryl and halogen, or R$^2$ and R$^3$, R$^3$ and R$^4$, R$^4$ and R$^5$, R$^6$ and R$^7$, R$^7$ and R$^8$, or, R$^8$ and R$^9$ together with the C-atoms, to which they are connected, form a 6 to 10 membered aromatic ring system, substituted 6 to 10 membered aromatic ring system, 5 to 12 membered heteroaromatic ring system or a substituted 5 to 12 membered heteroaromatic ring system, substituted $C_{1-30}$-alkyl, substituted $C_{2-30}$-alkenyl, substituted $C_{2-30}$-alkynyl, substituted O—$C_{1-30}$-alkyl and substituted S—$C_{1-30}$-alkyl, at each occurrence, are $C_{1-30}$-alkyl, $C_{2-30}$-alkenyl, $C_{2-30}$-alkynyl, O—$C_{1-30}$-alkyl, respectively, S—$C_{1-30}$-alkyl, which are substituted with at least one substituent independently selected from the group consisting of $C_{5-6}$-cycloalkyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—C(O)$R^b$, $NR^a$—C(O)—$OR^b$, $NR^a$—C(O)—$NR^bR^c$, $SR^a$, S—C(O)—$R^a$, halogen, CN, and $NO_2$;

substituted $C_{5-8}$-cycloalkyl, and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{2-20}$-alkenyl, $C_{2-20}$-alkynyl, $C_{5-6}$-cycloalkyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—C(O)$R^b$, $NR^a$—C(O)—$OR^b$, $NR^a$—C(O)—$NR^bR^c$, $SR^a$, S—C(O)—$R^a$, halogen, CN, and $NO_2$;

substituted $C_{6-14}$-aryl, substituted 5 to 15 membered heteroaryl, substituted 6 to 10 membered aromatic ring system, and substituted 5 to 12 membered heteroaromatic ring system, at each occurrence, are $C_{6-14}$-aryl, 5 to 15 membered heteroaryl, 6 to 10 membered aromatic ring system, respectively, 5 to 12 membered heteroaromatic ring system, which are substituted with at least one substituent independently selected from the group consisting of $C_{1-20}$-alkyl, $C_{2-20}$-alkenyl, $C_{2-20}$-alkynyl, $C_{5-6}$-cycloalkyl, $C_{5-6}$-cycloalkenyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—C(O)$R^b$, $NR^a$—C(O)—$OR^b$, $NR^aC(O)$—$NR^bR^c$, $SR^a$, S—C(O)—$R^a$, halogen, CN, and $NO_2$, at least one $CH_2$-group, but not adjacent $CH_2$-groups, of $C_{1-30}$-alkyl, substituted $C_{1-30}$-alkyl, $C_{2-30}$-alkenyl, substituted $C_{2-30}$-alkenyl, $C_{2-30}$-alkynyl, substituted $C_{2-30}$-alkynyl, $C_{5-8}$-cycloalkyl, substituted $C_{5-8}$-cycloalkyl, $C_{5-8}$-cycloalkenyl, substituted $C_{5-8}$-cycloalkenyl, O—$C_{1-30}$-alkyl, substituted O—$C_{1-30}$-alkyl, S—$C_{1-30}$-alkyl and substituted S—$C_{1-30}$-alkyl, can be replaced by a linking group selected from the group consisting of O, S, $NR^{12}$, CO, O—C(O), C(O)—O, O—C(O)—O, S—C(O), C(O)—S, $NR^{12}$—C(O), C(O)—$NR^{12}$, OC(O)—$NR^{12}$ and $NR^{12}$—C(O)—O, $R^{12}$ is H, $C_{1-30}$-alkyl, substituted $C_{1-30}$-alkyl, $C_{2-30}$-alkenyl, substituted $C_{2-30}$-alkenyl, $C_{2-30}$-alkynyl, substituted $C_{2-30}$-alkynyl or C(O)—$OR^d$, and $R^a$, $R^b$, $R^c$ and $R^d$ are independently from each other and at each occurrence selected from the group consisting of H, $C_{1-20}$-alkyl, $C_{2-20}$-alkenyl, $C_{2-20}$-alkynyl, $C_{5-6}$-cycloalkyl, $C_{5-6}$-cycloalkenyl, $C_{6-10}$-aryl, and 5 to 12 membered heteroaryl.

2. The compound of claim 1, wherein:

X is O, S or $NR^{10}$, $R^{10}$ is H, $C_{1-30}$-alkyl, substituted $C_{1-30}$-alkyl, $C_{2-30}$-alkenyl, substituted $C_{2-30}$-alkenyl, or C(O)—$OR^{11}$, $R^1$ and $R^{11}$ are independently from each other selected from the group consisting of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl, and substituted $C_{5-8}$-cycloalkenyl, $R^2$, $R^3$, $R^4$, $R^5$, $R^6$, $R^7$, $R^8$ and $R^9$ are independently from each other selected from the group consisting of H, $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl, substituted $C_{5-8}$-cycloalkenyl, O—$C_{1-30}$-alkyl, substituted O—$C_{1-30}$-alkyl, S—$C_{1-30}$-alkyl, substituted S—$C_{1-30}$-alkyl, $C_{6-14}$-aryl, substituted $C_{6-14}$-aryl, 5 to 15 membered heteroaryl, substituted 5 to 15 membered heteroaryl and halogen, or $R^2$ and $R^3$, $R^3$ and $R^4$, $R^4$ and $R^5$, $R^6$ and $R^7$, $R^7$ and $R^8$, or, $R^8$ and $R^9$ together with the C-atoms, to which they are connected, form a 6 to 10 membered aromatic ring system, substituted 6 to 10 membered aromatic ring system, 5 to 12 membered heteroaromatic ring system or a substituted 5 to 12 membered heteroaromatic ring system, substituted $C_{1-30}$-alkyl, substituted $C_{2-30}$-alkenyl, substituted O—$C_{1-30}$-alkyl and substituted S—$C_{1-30}$-alkyl, at each occurrence, are $C_{1-30}$-alkyl, $C_{2-30}$-alkenyl, O—$C_{1-30}$-alkyl, respectively, S—$C_{1-30}$-alkyl, which are substituted with at least one substituent independently selected from the group consisting of $C_{5-6}$-cycloalkyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—C(O)$R^b$, $NR^a$—C(O)—$OR^b$, $NR^a$—C(O)—$NR^bR^c$, $SR^a$, S—C(O)—$R^a$, halogen, CN, and $NO_2$;

substituted $C_{5-8}$-cycloalkyl, and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{5-6}$-cycloalkyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—C(O)$R^b$, $NR^a$—C(O)—$OR^b$, $NR^a$—C(O)—$NR^bR^c$, $SR^a$, S—C(O)—$R^a$, halogen, CN, and $NO_2$;

substituted $C_{6-14}$-aryl, substituted 5 to 15 membered heteroaryl, substituted 6 to 10 membered aromatic ring system, and substituted 5 to 12 membered heteroaromatic ring system, at each occurrence, are $C_{6-14}$-aryl, 5 to 15 membered heteroaryl, 6 to 10 membered aromatic ring system, respectively, 5 to 12 membered heteroaromatic ring system, which are substituted with at least one substituent independently selected from the group consisting of $C_{1-20}$-alkyl, $C_{5-6}$-cycloalkyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—

$C(O)R^b$, $NR^a$—$C(O)$—$OR^b$, $NR^aC(O)$—$NR^bR^c$, $SR^a$, S—C(O)—$R^a$, halogen, CN, and $NO_2$, at least one $CH_2$-group, but not adjacent $CH_2$-groups, of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl, and substituted $C_{5-8}$-cycloalkenyl, O—$C_{1-30}$-alkyl, substituted O—$C_{1-30}$-alkyl, S—$C_{1-30}$-alkyl and substituted S—$C_{1-30}$-alkyl, can be replaced by a linking group selected from the group consisting of O, S, $NR^{12}$, CO, O—C(O), C(O)—O, O—C(O)—O, S—C(O), C(O)—S, $NR^{12}$—C(O), C(O)—$NR^{12}$, OC(O)—$NR^{12}$ and $NR^{12}$—C(O)—O, $R^{12}$ is H, $C_{1-30}$-alkyl, substituted $C_{1-30}$-alkyl, or C(O)—$OR^d$, and $R^a$, $R^b$, $R^c$ and $R^d$ are independently from each other and at each occurrence selected from the group consisting of H, $C_{1-20}$-alkyl, $C_{5-6}$-cycloalkyl, $C_{6-10}$-aryl, and 5 to 12 membered heteroaryl.

3. The compound of claim 1, wherein:

X is O, S or $NR^{10}$, $R^{10}$ is H, $C_{1-30}$-alkyl, substituted $C_{1-30}$-alkyl or C(O)—$OR^{11}$, $R^1$ and $R^{11}$ are independently from each other selected from the group consisting of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl, and substituted $C_{5-8}$-cycloalkenyl, $R^2$, $R^3$, $R^4$, $R^5$, $R^6$, $R^7$, $R^8$ and $R^9$ are independently from each other selected from the group consisting of H, $C_{1-30}$-alkyl, substituted $C_{1-30}$-alkyl, $C_{5-8}$-cycloalkyl, substituted $C_{5-8}$-cycloalkyl, $C_{6-14}$-aryl, substituted $C_{6-14}$-aryl, 5 to 15 membered heteroaryl, substituted 5 to 15 membered heteroaryl and halogen, or $R^2$ and $R^3$, $R^3$ and $R^4$, $R^4$ and $R^5$, $R^6$ and $R^7$, $R^7$ and $R^8$, or, $R^8$ and $R^9$ together with the C-atoms, to which they are connected, form a 6 to 10 membered aromatic ring system, substituted 6 to 10 membered aromatic ring system, 5 to 12 membered heteroaromatic ring system or a substituted 5 to 12 membered heteroaromatic ring system, substituted $C_{1-30}$-alkyl, substituted $C_{2-30}$-alkenyl, at each occurrence, are $C_{1-30}$-alkyl, respectively, $C_{2-30}$-alkenyl, which are substituted with at least one substituent independently selected from the group consisting of $C_{5-6}$-cycloalkyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—$C(O)R^b$, $NR^a$—C(O)—$OR^b$, $NR^a$—C(O)—$NR^bR^c$, $SR^a$, S—C(O)—$R^a$, halogen, CN, and $NO_2$;

substituted $C_{5-8}$-cycloalkyl, and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{5-6}$-cycloalkyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—$C(O)R^b$, $NR^a$—C(O)—$OR^b$, $NR^a$—C(O)—$NR^bR^c$, $SR^a$, S—C(O)—$R^a$, halogen, CN, and $NO_2$;

substituted $C_{6-14}$-aryl, substituted 5 to 15 membered heteroaryl, substituted 6 to 10 membered aromatic ring system, and substituted 5 to 12 membered heteroaromatic ring system, at each occurrence, are $C_{6-14}$-aryl, 5 to 15 membered heteroaryl, 6 to 10 membered aromatic ring system, respectively, 5 to 12 membered heteroaromatic ring system, which are substituted with at least one substituent independently selected from the group consisting of $C_{1-20}$-alkyl, $C_{5-6}$-cycloalkyl, $C_{6-10}$-aryl, 5 to 12 membered heteroaryl, $OR^a$, OC(O)—$R^a$, OC(O)—$OR^a$, OC(O)—$NR^aR^b$, C(O)—$R^a$, C(O)—$OR^a$, C(O)—$NR^aR^b$, C(O)—$NR^a$—$NR^bR^c$, C(O)—$NR^a$—$OR^b$, C(O)—$NR^a$—C(O)—$R^b$, C(O)—$NR^a$—C(O)—$OR^b$, C(O)—$SR^a$, $NR^aR^b$, $NR^a$—$NR^bR^c$, $NR^a$—$C(O)R^b$, $NR^a$—C(O)—$OR^b$, $NR^aC(O)$—$NR^bR^c$, $SR^a$, S—C(O)—$R^a$, halogen, CN, and $NO_2$, at least one $CH_2$-group, but not adjacent $CH_2$-groups, of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl, and substituted $C_{5-8}$-cycloalkenyl can be replaced by a linking group selected from the group consisting of O, S, $NR^{12}$, CO, O—C(O), C(O)—O, O—C(O)—O, S—C(O), C(O)—S, $NR^{12}$—C(O), C(O)—$NR^{12}$, OC(O)—$NR^{12}$ and $NR^{12}$—C(O)—O, $R^{12}$ is H, $C_{1-30}$-alkyl, substituted $C_{1-30}$-alkyl, or C(O)—$OR^d$, $R^a$, $R^b$, $R^c$ and $R^d$ are independently from each other and at each occurrence selected from the group consisting of H, $C_{1-20}$-alkyl, $C_{5-6}$-cycloalkyl, $C_{6-10}$-aryl, and 5 to 12 membered heteroaryl.

4. The compound of claim 1, wherein:

X is O, S or $NR^{10}$, $R^{10}$ is H, $C_{1-30}$-alkyl, substituted $C_{1-30}$-alkyl or C(O)—$OR^{11}$, $R^1$ and $R^{11}$ are independently from each other selected from the group consisting of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl, and substituted $C_{5-8}$-cycloalkenyl, $R^2$, $R^3$, $R^4$, $R^5$, $R^6$, $R^7$, $R^8$ and $R^9$ are independently from each other selected from the group consisting of H, $C_{1-30}$-alkyl, substituted $C_{1-30}$-alkyl, $C_{5-8}$-cycloalkyl, substituted $C_{5-8}$-cycloalkyl, $C_{6-14}$-aryl, substituted $C_{6-14}$-aryl, 5 to 15 membered heteroaryl and substituted 5 to 15 membered heteroaryl; or $R^2$ and $R^3$, $R^3$ and $R^4$, $R^4$ and $R^5$, $R^6$ and $R^7$, $R^7$ and $R^8$, or, $R^8$ and $R^9$ together with the C-atoms, to which they are connected, form a 6 to 10 membered aromatic ring system, substituted 6 to 10 membered aromatic ring system, 5 to 12 membered heteroaromatic ring system or a substituted 5 to 12 membered heteroaromatic ring system, substituted $C_{1-30}$-alkyl, substituted $C_{2-30}$-alkenyl, at each occurrence, are $C_{1-30}$-alkyl, respectively, $C_{2-30}$-alkenyl, which are substituted with at least one substituent independently selected from the group consisting of $C_{5-6}$-cycloalkyl, $C_{6-10}$-aryl, 5 to 12 membered heteroaryl, substituted $C_{5-8}$-cycloalkyl, and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{5-6}$-cycloalkyl, $C_{6-10}$-aryl, 5 to 12 membered heteroaryl;

substituted $C_{6-14}$-aryl, substituted 5 to 15 membered heteroaryl, substituted 6 to 10 membered aromatic ring system, and substituted 5 to 12 membered heteroaromatic ring system, at each occurrence, are $C_{6-14}$-aryl, 5 to 15 membered heteroaryl, 6 to 10 membered aromatic ring system, respectively, 5 to 12 membered heteroaromatic ring system, which are substituted with at least one substituent independently selected from the group consisting of $C_{1-20}$-alkyl, $C_{5-6}$-cycloalkyl, $C_{6-10}$-aryl, 5 to 12 membered heteroaryl;

at least one $CH_2$-group, but not adjacent $CH_2$-groups, of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl, and substituted $C_{5-8}$-cycloalkenyl can be replaced by a linking group selected from the group consisting of O, S, $NR^{12}$, $R^{12}$ is H, $C_{1-30}$-alkyl, substituted $C_{1-30}$-alkyl or C(O)—$OR^d$, and $R^d$ is at each occurrence selected from the group consisting of H, $C_{1-20}$-alkyl, $C_{2-20}$-alkenyl, $C_{2-20}$-alkynyl, $C_{5-6}$-cycloalkyl, $C_{5-6}$-cycloalkenyl, $C_{6-10}$-aryl, and 5 to 12 membered heteroaryl.

5. The compound of claim 1, wherein:

X is S, $R^1$ is selected from the group consisting of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl and substituted $C_{5-8}$-cycloalkenyl, $R^2$, $R^3$, $R^4$, $R^5$, $R^6$, $R^7$, $R^8$ and $R^9$ are independently from each other selected from the group consisting of H, $C_{1-30}$-alkyl, substituted $C_{1-30}$-alkyl, $C_{5-8}$-cycloalkyl, substituted $C_{5-8}$-cycloalkyl, $C_{6-10}$-aryl, substituted $C_{6-10}$-aryl, 5 to 12 membered heteroaryl, and substituted 5 to 12 membered heteroaryl; or $R^2$ and $R^3$, $R^3$ and $R^4$, $R^4$ and $R^5$, $R^6$ and $R^7$, $R^7$ and $R^8$, or, $R^8$ and $R^9$ together with the C-atoms, to which they are connected, form a 6 membered aromatic ring system, substituted 6 membered aromatic ring system, 5 to 9 membered heteroaromatic ring system or a substituted 5 to 9 membered heteroaromatic ring system, substituted $C_{1-30}$-alkyl and substituted $C_{2-30}$-alkenyl, at each occurrence, are $C_{1-30}$-alkyl, respectively, $C_{2-30}$-alkenyl, which are substituted with at least one substituent independently selected from the group consisting of $C_{5-6}$-cycloalkyl, phenyl and 5 to 9 membered heteroaryl, substituted $C_{5-8}$-cycloalkyl and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{5-6}$-cycloalkyl, phenyl and 5 to 9 membered heteroaryl, substituted $C_{6-10}$-aryl, substituted 5 to 12 membered heteroaryl, substituted 6 membered aromatic ring system, and substituted 5 to 9 membered heteroaromatic ring system, at each occurrence, are $C_{6-10}$-aryl, 5 to 12 membered heteroaryl, 6 membered aromatic ring system, respectively, 5 to 9 membered heteroaromatic ring system, which are substituted with at least one substituent independently selected from the group consisting of $C_{1-20}$-alkyl, $C_{5-6}$-cycloalkyl, phenyl, 5 to 9 membered heteroaryl, and at least one $CH_2$-group, but not adjacent $CH_2$-groups, of $C_{1-30}$-alkyl, substituted $C_{1-30}$-alkyl, $C_{5-8}$-cycloalkyl and substituted $C_{5-8}$-cycloalkyl, can be replaced by the linking group O.

6. The compound of claim 1, wherein:

X is S, $R^1$ is selected from the group consisting of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl and substituted $C_{5-8}$-cycloalkenyl, $R^2$, $R^3$, $R^4$, $R^5$, $R^6$, $R^7$, $R^8$ and $R^9$ are independently from each other selected from the group consisting of H, $C_{1-30}$-alkyl, substituted $C_{1-30}$-alkyl, $C_{5-8}$-cycloalkyl, substituted $C_{5-8}$-cycloalkyl, substituted $C_{1-30}$-alkyl and substituted $C_{2-30}$-alkenyl, at each occurrence, are $C_{1-30}$-alkyl, respectively, $C_{2-30}$-alkenyl, which are substituted with at least one substituent independently selected from the group consisting of $C_{5-6}$-cycloalkyl, phenyl and 5 to 9 membered heteroaryl, and substituted $C_{5-8}$-cycloalkyl and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{5-6}$-cycloalkyl, phenyl and 5 to 9 membered heteroaryl.

7. The compound of claim 1, wherein:

X is S, $R^1$ is selected from the group consisting of $C_{1-30}$-alkyl, substituted $C_{1-30}$-alkyl, $C_{2-30}$-alkenyl, substituted $C_{2-30}$-alkenyl, $C_{5-8}$-cycloalkyl, substituted $C_{5-8}$-cycloalkyl, $C_{5-8}$-cycloalkenyl and substituted $C_{5-8}$-cycloalkenyl, $R^2$, $R^4$, $R^5$, $R^6$, $R^7$ and $R^9$ are H, $R^3$ and $R^8$ are independently from each other selected from the group consisting of H, $C_{1-30}$-alkyl, substituted $C_{1-30}$-alkyl, $C_{5-8}$-cycloalkyl and substituted $C_{5-8}$-cycloalkyl, substituted $C_{1-30}$-alkyl and substituted $C_{2-30}$-alkenyl, at each occurrence, are $C_{1-30}$-alkyl, respectively, $C_{2-30}$-alkenyl, which are substituted with at least one substituent independently selected from the group consisting of $C_{5-6}$-cycloalkyl and phenyl, and substituted $C_{5-8}$-cycloalkyl and substituted $C_{5-8}$-cycloalkenyl, at each occurrence, are $C_{5-8}$-cycloalkyl, respectively, $C_{5-8}$-cycloalkenyl, which are substituted with at least one substituent independently selected from the group consisting of $C_{1-20}$-alkyl, $C_{5-6}$-cycloalkyl and phenyl.

8. A process for preparing the compound of claim 1, the process comprising treating a compound of formula (2):

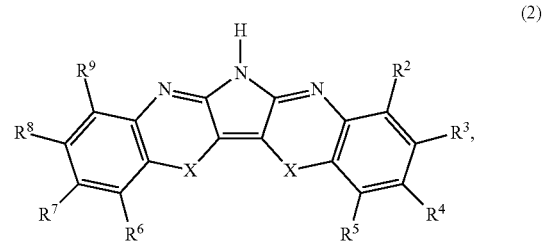

(2)

with a compound of formula:

$R^1O$—C(O)-LG to obtain the compound of formula (1):

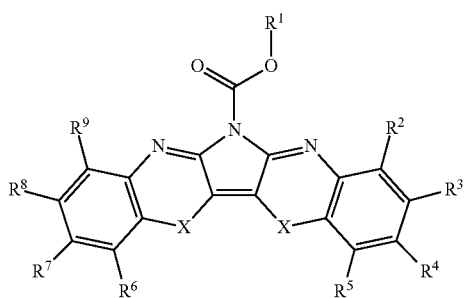

wherein:
X is O, S or NR$^{10}$,
R$^{10}$ is H, C$_{1-30}$-alkyl, substituted C$_{1-30}$-alkyl, C$_{2-30}$-alkenyl, substituted C$_{2-30}$-alkenyl, C$_{2-30}$-alkynyl, substituted C$_{2-30}$-alkynyl or C(O)—OR$^{11}$;
R$^1$ and R$^{11}$ are independently from each other selected from the group consisting of C$_{1-30}$-alkyl, substituted C$_{1-30}$-alkyl, C$_{2-30}$-alkenyl, substituted C$_{2-30}$-alkenyl, C$_{2-30}$-alkynyl, substituted C$_{2-30}$-alkynyl, C$_{5-8}$-cycloalkyl, substituted C$_{5-8}$-cycloalkyl, C$_{5-8}$-cycloalkenyl, and substituted C$_{5-8}$-cycloalkenyl;
R$^2$, R$^3$, R$^4$, R$^5$, R$^6$, R$^7$, R$^8$ and R$^9$ are independently from each other selected from the group consisting of H, C$_{1-30}$-alkyl, substituted C$_{1-30}$-alkyl, C$_{2-30}$-alkenyl, substituted C$_{2-30}$-alkenyl, C$_{2-30}$-alkynyl, substituted C$_{2-30}$-alkynyl, C$_{5-8}$-cycloalkyl, substituted C$_{5-8}$-cycloalkyl, C$_{5-8}$-cycloalkenyl, substituted C$_{5-8}$-cycloalkenyl, O—C$_{1-30}$-alkyl, substituted O—C$_{1-30}$-alkyl, S—C$_{1-30}$-alkyl, substituted S—C$_{1-30}$-alkyl, C$_{6-14}$-aryl, substituted C$_{6-14}$-aryl, 5 to 15 membered heteroaryl, substituted 5 to 15 membered heteroaryl and halogen,
or R$^2$ and R$^3$, R$^3$ and R$^4$, R$^4$ and R$^5$, R$^6$ and R$^7$, R$^7$ and R$^8$, or, R$^8$ and R$^9$ together with the C-atoms, to which they are connected, form a 6 to 10 membered aromatic ring system, substituted 6 to 10 membered aromatic ring system, 5 to 12 membered heteroaromatic ring system or a substituted 5 to 12 membered heteroaromatic ring system;
substituted C$_{1-30}$-alkyl, substituted C$_{2-30}$-alkenyl, substituted C$_{2-30}$-alkynyl, substituted O—C$_{1-30}$-alkyl and substituted S—C$_{1-30}$-alkyl, at each occurrence, are C$_{1-30}$-alkyl, C$_{2-30}$-alkenyl, C$_{2-30}$-alkynyl, O—C$_{1-30}$-alkyl, respectively, S—C$_{1-30}$-alkyl, which are substituted with at least one substituent independently selected from the group consisting of C$_{5-6}$-cycloalkyl, C$_{6-10}$-aryl, 5 to 12 membered heteroaryl, OR$^a$, OC(O)—R$^a$, OC(O)—OR$^a$, OC(O)—NR$^a$R$^b$, C(O)—R$^a$, C(O)—OR$^a$, C(O)—NR$^a$R$^b$, C(O)—NR$^a$—NR$^b$R$^c$, C(O)—NR$^a$—OR$^b$, C(O)—NR$^a$—C(O)—R$^b$, C(O)—NR$^a$—C(O)—OR$^b$, C(O)—SR$^a$, NR$^a$R$^b$, NR$^a$—NR$^b$R$^c$, NR$^a$—C(O)R$^b$, NR$^a$—C(O)—OR$^b$, NR$^a$—C(O)—NR$^b$R$^c$, SR$^a$, S—C(O)—R$^a$, halogen, CN, and NO$_2$;
substituted C$_{5-8}$-cycloalkyl, and substituted C$_{5-8}$-cycloalkenyl, at each occurrence, are C$_{5-8}$-cycloalkyl, respectively, C$_{5-8}$-cycloalkenyl, which are substituted with at least one substituent independently selected from the group consisting of C$_{1-20}$-alkyl, C$_{2-20}$-alkenyl, C$_{2-20}$-alkynyl, C$_{5-6}$-cycloalkyl, C$_{6-10}$-aryl, 5 to 12 membered heteroaryl, OR$^a$, OC(O)—R$^a$, OC(O)—OR$^a$, OC(O)—NR$^a$R$^b$, C(O)—R$^a$, C(O)—OR$^a$, C(O)—NR$^a$R$^b$, C(O)—NR$^a$—NR$^b$R$^c$, C(O)—NR$^a$—OR$^b$, C(O)—NR$^a$—C(O)—R$^b$, C(O)—NR$^a$—C(O)—OR$^b$, C(O)—SR$^a$, NR$^a$R$^b$, NR$^a$—NR$^b$R$^c$, NR$^a$—C(O) R$^b$, NR$^a$—C(O)—OR$^b$, NR$^a$—C(O)—NR$^b$R$^c$, SR$^a$, S—C(O)—R$^a$, halogen, CN, and NO$_2$;
substituted C$_{6-14}$-aryl, substituted 5 to 15 membered heteroaryl, substituted 6 to 10 membered aromatic ring system, and substituted 5 to 12 membered heteroaromatic ring system, at each occurrence, are C$_{6-14}$-aryl, 5 to 15 membered heteroaryl, 6 to 10 membered aromatic ring system, respectively, 5 to 12 membered heteroaromatic ring system, which are substituted with at least one substituent independently selected from the group consisting of C$_{1-20}$-alkyl, C$_{2-20}$-alkenyl, C$_{2-20}$-alkynyl, C$_{5-6}$-cycloalkyl, C$_{5-6}$-cycloalkenyl, C$_{6-10}$-aryl, 5 to 12 membered heteroaryl, OR$^a$, OC(O)—R$^a$, OC(O)—OR$^a$, OC(O)—NR$^a$R$^b$, C(O)—R$^a$, C(O)—OR$^a$, C(O)—NR$^a$R$^b$, C(O)—NR$^a$—NR$^b$R$^c$, C(O)—NR$^a$—OR$^b$, C(O)—NR$^a$—C(O)—R$^b$, C(O)—NR$^a$—C(O)—OR$^b$, C(O)—SR$^a$, NR$^a$R$^b$, NR$^a$—NR$^b$R$^c$, NR$^a$—C(O) R$^b$, NR$^a$—C(O)—OR$^b$, NR$^a$C(O)—NR$^b$R$^c$, SR$^a$, S—C(O)—R$^a$, halogen, CN, and NO$_2$;
at least one CH$_2$-group, but not adjacent CH$_2$-groups, of C$_{1-30}$-alkyl, substituted C$_{1-30}$-alkyl, C$_{2-30}$-alkenyl, substituted C$_{2-30}$-alkenyl, C$_{2-30}$-alkynyl, substituted C$_{2-30}$-alkynyl, C$_{5-8}$-cycloalkyl, substituted C$_{5-8}$-cycloalkyl, C$_{5-8}$-cycloalkenyl, substituted C$_{5-8}$-cycloalkenyl, O—C$_{1-30}$-alkyl, substituted O—C$_{1-30}$-alkyl, S—C$_{1-30}$-alkyl and substituted S—C$_{1-30}$-alkyl, can be replaced by a linking group selected from the group consisting of O, S, NR$^{12}$, CO, O—C(O), C(O)—O, O—C(O)—O, S—C(O), C(O)—S, NR$^{12}$—C(O), C(O)—NR$^{12}$, OC(O)—NR$^{12}$ and NR$^{12}$—C(O)—O;
R$^{12}$ is H, C$_{1-30}$-alkyl, substituted C$_{1-30}$-alkyl, C$_{2-30}$-alkenyl, substituted C$_{2-30}$-alkenyl, C$_{2-30}$-alkynyl, substituted C$_{2-30}$-alkynyl or C(O)—OR$^d$;
R$^a$, R$^b$, R$^c$ and R$^d$ are independently from each other and at each occurrence selected from the group consisting of H, C$_{1-20}$-alkyl, C$_{2-20}$-alkenyl, C$_{2-20}$-alkynyl, C$_{5-6}$-cycloalkyl, C$_{5-6}$-cycloalkenyl, C$_{6-10}$-aryl, and 5 to 12 membered heteroaryl; and
LG is a leaving group.

9. An electronic device, comprising the compound of claim 1, wherein said electronic device is an organic photovoltaic device (OPV), an organic field-effect transistor (OFET), an organic light emitting diode (OLED), or an organic photodiode (OPD).

10. The electronic device of claim 9, wherein the electronic device is an organic field effect transistor (OFET).

11. A semiconducting material, comprising the compound of claim 1.

* * * * *

UNITED STATES PATENT AND TRADEMARK OFFICE
CERTIFICATE OF CORRECTION

PATENT NO. : 10,079,346 B2
APPLICATION NO. : 15/537522
DATED : September 18, 2018
INVENTOR(S) : Hitoshi Yamato et al.

It is certified that error appears in the above-identified patent and that said Letters Patent is hereby corrected as shown below:

On the Title Page

Column 2, Item (57) Abstract, Line 4, "C(0)-OR$^{11}$," should read --C(O)-OR$^{11}$,--;

In the Specification

Column 11, Lines 1-2, "NR$^a$C(O)-NR$^b$R$^c$," should read --NR$^a$-C(O)-NR$^b$R$^c$,--;

Column 11, Lines 13-14, "C(O)NR$^a$-OR$^b$," should read --C(O)-NR$^a$-OR$^b$,--;

Column 11, Lines 15-16, "NR$^a$C(O)-R$^b$," should read --NR$^a$-C(O)-R$^b$,--;

Column 12, Line 11, "NR$^a$C(O)-NR$^b$R$^c$," should read --NR$^a$-C(O)-NR$^b$R$^c$,--;

Column 12, Lines 24-25, "C(O)NR$^a$-OR$^b$," should read --C(O)-NR$^a$-OR$^b$,--;

Column 12, Lines 26-27, "NR$^a$C(O)R$^b$," should read --NR$^a$-C(O)R$^b$,--;

Column 16, Line 20, "NR$^a$C(O)-NR$^b$R$^c$," should read --NR$^a$-C(O)-NR$^b$R$^c$,--;

In the Claims

Column 36, Claim 2, Line 4, "substituted C$_{2-30}$-alkenyl, or C(O)-OR$^{11}$," should read --substituted C$_{2-30}$-alkenyl or C(O)-OR$^{11}$,--;

Column 36, Claim 2, Lines 8-9, "C$_{5-8}$-cycloalkenyl, and substituted" should read --C$_{5-8}$-cycloalkenyl and substituted--;

Column 36, Claim 2, Line 15, "C$_{5-8}$-cycloalkenyl, substituted" should read --C$_{5-8}$-cycloalkenyl and substituted--;

Signed and Sealed this
Twenty-second Day of October, 2019

Andrei Iancu
*Director of the United States Patent and Trademark Office*

CERTIFICATE OF CORRECTION (continued)
U.S. Pat. No. 10,079,346 B2

Column 36, Claim 2, Line 20, "and halogen," should read --and halogen;--;

Column 36, Claim 2, Line 41, "substituted $C_{5-8}$-cycloalkyl, and substituted" should read --substituted $C_{5-8}$-cycloalkyl and substituted--;

Column 37, Claim 2, Line 6, "$C_{5-8}$-cycloalkenyl, substituted" should read --$C_{5-8}$-cycloalkenyl substituted--;

Column 37, Claim 3, Lines 27-28, "$C_{5-8}$-cycloalkenyl, and substituted" should read --$C_{5-8}$-cycloalkenyl and substituted--;

Column 37, Claim 3, Line 33, "heteroaryl," should read --heteroaryl and--;

Column 37, Claim 3, Line 34, "to 15 membered heteroaryl and halogen" should read --to 15 membered heteroaryl;--;

Column 37, Claim 3, Line 41, "substituted $C_{1-30}$-alkyl, substituted" should read --substituted $C_{1-30}$-alkyl and substituted--;

Column 37, Claim 3, Line 53, "substituted $C_{5-8}$-cycloalkyl, and substituted" should read --substituted $C_{5-8}$-cycloalkyl and substituted--;

Column 38, Claim 3, Line 18, "$C_{5-8}$-cycloalkyl, $C_{5-8}$-cycloalkenyl" should read --$C_{5-8}$-cycloalkyl $C_{5-8}$-cycloalkenyl--;

Column 38, Claim 3, Line 24, "substituted $C_{1-30}$-alkyl, or" should read --substituted $C_{1-30}$-alkyl or--;

Column 38, Claim 4, Lines 37-38, "$C_{5-8}$-cycloalkenyl, and substituted" should read --$C_{5-8}$-cycloalkenyl and substituted--;

Column 38, Claim 4, Line 51, "substituted $C_{1-30}$-alkyl, substituted" should read --substituted $C_{1-30}$-alkyl and substituted--;

Column 38, Claim 4, Line 57, "substituted $C_{5-8}$-cycloalkyl, and substituted" should read --substituted $C_{5-8}$-cycloalkyl and substituted--;

Column 39, Claim 4, Line 9, "$C_{5-8}$-cycloalkenyl, and substituted" should read --$C_{5-8}$-cycloalkenyl and substituted--.